(12) United States Patent
Burger et al.

(10) Patent No.: US 11,011,266 B2
(45) Date of Patent: May 18, 2021

(54) HEALTH PROVIDER MATCHING SERVICE

(71) Applicant: Lyra Health, Inc., Burlingame, CA (US)

(72) Inventors: Jessie M. Burger, Mountain View, CA (US); Daniella J. Perlroth, Palo Alto, CA (US); Aaron Archer Waterman, Mountain View, CA (US)

(73) Assignee: LYRA HEALTH, INC., Burlingame, CA (US)

( * ) Notice: Subject to any disclaimer, the term of this patent is extended or adjusted under 35 U.S.C. 154(b) by 618 days.

(21) Appl. No.: 15/172,435

(22) Filed: Jun. 3, 2016

(65) Prior Publication Data

US 2017/0351830 A1 Dec. 7, 2017

(51) Int. Cl.
*G16H 40/20* (2018.01)
*G16H 80/00* (2018.01)
*G16H 20/00* (2018.01)

(52) U.S. Cl.
CPC ............ *G16H 40/20* (2018.01); *G16H 20/00* (2018.01); *G16H 80/00* (2018.01)

(58) Field of Classification Search
CPC ......... G06F 19/00; G16H 80/00; G16H 40/20
USPC ........................................................... 705/2
See application file for complete search history.

(56) References Cited

U.S. PATENT DOCUMENTS

| | | | | |
|---|---|---|---|---|
| 2003/0167265 | A1* | 9/2003 | Corynen | G06Q 10/04 |
| 2009/0182755 | A1* | 7/2009 | Adair | G06F 16/22 |
| 2009/0259488 | A1* | 10/2009 | Gounares | G06Q 10/06 705/3 |
| 2011/0301982 | A1* | 12/2011 | Green, Jr. | G06Q 10/06 705/3 |
| 2014/0350954 | A1* | 11/2014 | Ellis | G16H 50/20 705/2 |
| 2016/0256690 | A1* | 9/2016 | Cecchi | A61N 1/36132 |

\* cited by examiner

*Primary Examiner* — Robert A Sorey
*Assistant Examiner* — Kimberly A. Sass
(74) *Attorney, Agent, or Firm* — Fenwick & West LLP

(57) ABSTRACT

A health provider matching service is provided to match patients to health providers based on a semantic relationship graph of data associated with conditions of patients. Using natural language processing, the service identifies terms describing symptoms, treatments, and health providers associated with a condition. The service then identifies semantic relations among the terms and probability distributions of the terms to generate a semantic relationship graph. Quality information of therapists is combined with machine learning techniques to identify features that are used to distinguish high quality and low quality providers. Based on the semantic relationship graph and the derived quality information, the service matches a patient to a health provider suitable to treat the particular needs of the patient. The service also handles social, behavioral, or emotional issues for which medications are not appropriate.

20 Claims, 14 Drawing Sheets

1: Generalized anxiety disorder
2:
3: Anxiety disorders are emotional disorders that include symptoms such as:
4: - Being exhausted all of the time
5: - Feeling queasy
6: - Feeling nauseated
7: - Physical symptoms such as tingling in the hands or numbness.
8:
9: Therapies include:
10: - Acceptance commitment
11: - Cognitive behavior modification
12:
13: Medications include:
14: - Lexapro
15: - Neurontin
16:

300

Medications
700

Gabapentin
710

| Gabapentin 711 | 100% |
| Neogab 451 | 90% |
| Neurontin 332 | 80% |

Escitalopram
720

| Escitalopram 721 | 100% |
| Escitalopram oxalate 722 | 90% |
| Lexapro 331 | 80% |

FIG. 7

HEALTH PROVIDER MATCHING SERVICE

BACKGROUND

This disclosure relates generally to a service that matches health providers to medical needs of patients, and particularly to health provider-to-patient matching using a semantic relationship graph including quality information about health providers and semantically related medical terms.

Digital computing has empowered patient care by providing more personalized and precise patient care. One important aspect of providing personalized health care is finding competent health care providers for a given patient according to the patient's medical conditions and preferences for treatment. Behavioral health is one area in particular where it has been difficult or impossible for patients to find the right psychiatrist, therapist, or the like for effective diagnosis of behavioral health conditions of the patients.

Taking therapy as an example, therapy for behavioral health conditions is often a more personal treatment option, which makes finding an appropriate therapist significantly more difficult than identifying a medication provider. Therapists typically describe their treatment approaches and philosophies in personal statements on their practice websites and/or other professional association websites, e.g., PSYCHOLOGYTODAY, HEALTHGRADES, ZOCDOC™, GOODTHERAPY®, but this data is unstructured, is not normalized across therapists, and varies by depending on the source. For example, some websites may have barebones information including only health providers' names and contact information. On the other hand, other websites may have a more detailed list of therapies offered and conditions treated. The unstructured and incomplete nature of the available information about health providers calls for a new approach to aggregate unstructured data found on sources such as practice websites to help patients find a suitable health provider.

SUMMARY

A health provider matching service is provided to match patients to health providers based on a semantic relationship graph of data associated with conditions. Using natural language processing, the service identifies terms (e.g., terms describing symptoms, treatments, medications, therapies, and providers) associated with a medical condition, behavioral issue, emotional issue, or social issue commonly used by health providers and/or patients from resources targeted at health care professionals and/or laypeople. The service then identifies semantic relations among the terms, e.g., whether two terms are synonyms, to generate a semantic relationship graph. For example, terms cognitive behavioral psychotherapy and cognitive behavior modification are semantically related because both terms refer to a cognitive behavioral therapy. The service applies clinical guidelines to derive quality information about health providers, e.g., information indicating whether a therapist provides high quality or low quality treatment to patients. For instance, clinical guidelines indicate that evidence-based treatments methodologies are high quality treatments. The service determines adherence of a health provider to evidence-based methodologies for the medical condition by analyzing terms in the graph connected to the health provider in context of the clinical guidelines. The derived quality information can be combined with machine learning techniques to identify terms that are more frequently used by high quality and/or low quality providers. Based on the semantic relationship graph and the derived quality information, the service matches health providers to patients and refers the matched health providers to patients to treat their medical conditions or other types of issues.

BRIEF DESCRIPTION OF THE DRAWINGS

FIG. 7 is a diagram of key terms associated with a cluster of example medications organized by the health provider matching service according to one embodiment.

DETAILED DESCRIPTION

System Overview

Figure 1:
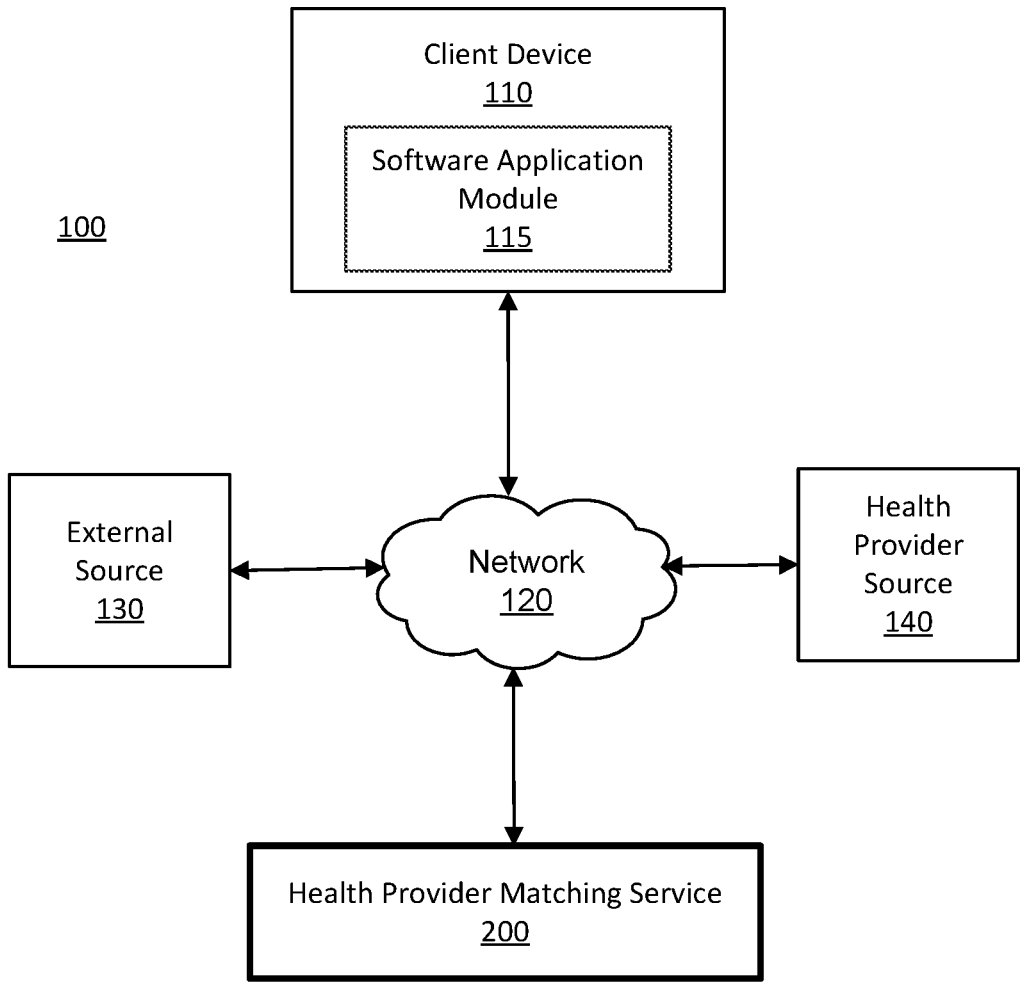
FIG. 1 is a block diagram of a computing environment for matching health providers to patients with a health provider matching service according to one embodiment.

FIG. 1 is a block diagram of a computing environment 100 for referring therapists to patients with a health provider matching service 200 according to one embodiment. Health providers may also be referred to as health care providers, providers, therapists, physicians, and psychiatrists herein. Based on a condition of a patient, health providers provide treatments, which can include therapy type treatment (also referred to as therapy), medication type treatment, among other types of treatment. Conditions include medical type conditions, as well as social issues, behavioral issues, and emotional issues. Conditions may also be referred to as medical conditions. The embodiment illustrated in FIG. 1 includes a client device 110 with a software application module 115, a health provider matching service 200, health provider source 140, and an external source 130 connected to each other by a network 120. Embodiments of the computing environment 100 can have multiple client devices 110 each with a software application module 115, therapist matching services 200, health provider sources 140, and external sources 130 connected to the network 120. Likewise, the functions performed by the various entities of FIG. 1 may differ in different embodiments.

A client device 110 is an electronic device used by a user to perform functions such as requesting best matched therapists based on a patient's personal medical needs, executing software applications, consuming digital content, browsing websites hosted by web servers on the network 120, downloading files, and the like. For example, the client device 110 may be a mobile device, a tablet, a notebook, a desktop computer, or a portable computer. The client device 110 includes interfaces with a display device on which the user may view webpages, videos and other content. In addition, the client device 110 provides a user interface (UI), such as physical and/or on-screen buttons with which the user may interact with the client device 110 to perform functions such as viewing, selecting, and consuming digital content such as digital medical records, webpages, photos, videos and other content. The user may be the patient himself or herself, family, friends, caregivers, clinicians, practitioners, hospitals, a health care service, a skilled nursing facility, an ambulatory surgical center, and some combination thereof or another person associated with the patient.

In one embodiment, the client device 110 has a software application module 115 for executing a health provider matching software application configured to refer an appropriate health provider to a patient based on user input, external sources, and providers. The software application may instruct the user to provide user input such as information including the patient's demographic data, preferred therapies, geographical location, medical history, and the like. The software application is executed to provide the user input to the health provider matching service 200 to identify appropriate therapists for referral and to receive the identified therapists' information from the health provider matching service 200. For example, upon executing the software application installed in the client device 110, the software application module 115 communicates with the health provider matching service 200 to send a request for therapists matched with a patient using the client device 110. Upon receiving the identified therapists' information from the health provider matching service 200, the software application module 115 presents the therapists' information to the patient in an intuitive and user friendly way, e.g., showing the location of an identified provider on a map next to the provider's contact information and web link.

The software application module 115 can be similarly installed and executed on computing devices associated with additional users who have been granted permission to participate in using the health provider matching service 200 on behalf of the patient. The software application module 115 can be a standalone application that a user downloads and uses on a client device 110, an online application accessed from an internet browser, or an application integrated into an employee health plan or wellness program at a company at which the patient is employed. In the latter case, the company may also have a software application installed on company devices through which a benefits team can interact with and manage this benefit for employees. Similarly, providers can have software applications installed on their devices or devices associated with their healthcare facility that allow providers to track their patients. The software application module 115 presents a user friendly interface for guiding the user to find therapists appropriate for the patient using the therapist matching software application executed on the client device 110. The user's input is considered by the health provider matching service 200 to find appropriate therapist for the patient.

The network 120 enables communications among network entities such as the client device 110, the health provider matching service 200, the external source 130, and the health provider source 140. In one embodiment, the network 120 comprises the Internet and uses standard communications technologies and/or protocols, e.g., BLUETOOTH®, WiFi, ZIGBEE®, clouding computing, other air to air, wire to air networks, and mesh network protocols to client devices, gateways, and access points. In another embodiment, the network entities can use custom and/or dedicated data communications technologies.

In one embodiment, the external source 130 provides information that facilitates the therapist matching performed by the health provider matching service 200. The database of the external source 130 may also store medical practice standards (e.g., prescribing guidelines of consensus practice recommendations for different treatments and medication for different medical conditions), information targeted to health care professionals (e.g., DSM-5, ICD-9, ICD-10, and UPTODATE®), and information targeted to laypeople (e.g., Wikipedia, Drugbank, RxWiki, PsychologyToday, GoodTherapy®, and WebMD®). In some embodiments, the information collected from the external source 130 is collected each time a therapist matching is conducted and is utilized in that matching. In other embodiments, the health provider matching service 200 builds up one or more of its own databases (e.g., see FIG. 2) of information about providers either in advance or as matches are performed such that the health provider matching service 200 can utilize its own source of information about providers. Such a therapist matching database can be updated regularly to ensure the most accurate and up-to-date information can be used by the health provider matching service 200.

The external source 130 may also include historical health data of a patient (e.g., a patient's electronic medical records, or EMRs) from various health record sources (e.g., hospital records, records at the patient's family doctors, or manually inputted data related to the patient's health by the patient's caretakers). The historical health data of a patient describes a global view of the patient's lifestyle and wellness. Further, the historical health data of a patient can be used in the therapist matching process for the patient.

In one embodiment, the health provider source 140 includes one or more databases storing information about health providers (e.g., PSYCHOLOGYTODAY, GOODTHERAPY®, HEALTHGRADES®, National Provider Identifier (NPI) provided by National Plan & Provider Enumeration System (NPPES), and ZOCDOC™), U.S. physician prescribing data (i.e., drugs prescription) provided by First DataBank, Medicare Part D and IMS HEALTH™, patient statistics and evidence-based treatments (e.g., provided by online resources such as UPTODATE®, SK&A, LEXISNEXIS®, and web crawling), and personal websites of therapists. The information about providers from personal websites may include therapists' preferred therapies, preferred medications, target clients, conditions treated, geographical location, contact information, medical experience, and training. A profile associated with a therapist on the one or more databases may include a link to a personal website of the therapist. The health provider matching service 200 can retrieve unstructured data from the health provider source 140 for use in generating a semantic relationship graph, which provides quality information about therapists and semantically related medical terms used for therapists matching.

The health provider matching service 200 processes the user input, data from the health provider source 140, data from the external source 130, and/or data from a local database, and identifies therapists that match the needs of the patient based on the processed information. In one embodiment, the health provider matching service 200 identifies semantically related terms, which are commonly used by behavioral health therapists and/or patients, e.g., using natural language processing techniques to analyze health information available from resources targeted at health care professionals and educational resources targeted at laypeople. The identified terms are related to different categories of health information also referred to herein as clusters, e.g., conditions, symptoms, medications, therapies, and providers. Each cluster includes one or more key terms associated with the cluster. For example, the "conditions" cluster includes key term, generalized anxiety disorder; the "symptoms" cluster includes key term, nausea; the "medications" cluster includes key term Gabapentin; the "therapies" cluster includes key term, cognitive behavioral therapy; the "providers" cluster includes key term, Dr. Grace Hopper. The health provider matching service 200 further identifies connections between key terms of clusters. For example, a condition is connected to a symptom if patients diagnosed with the condition typically experience the symptom; a condition is connected to a medication if patients diagnosed with the condition typically take the medication to treat the condition; a condition is connected to a therapy if patients diagnosed with the condition typically undergo the therapy to treat the condition; a condition is connected to a provider if the provider typically treats patients diagnosed with the condition. In one embodiment, the health provider matching service 200 describes the semantic relations among the semantically related terms and key terms in a semantic relationship graph. The health provider matching service 200 extracts a vector representation of therapist data, e.g., a word vector representation of semantically related terms and key terms. The health provider matching service 200 applies clinical guidelines to the therapist data to derive quality information of therapists that is analyzed by the health provider matching service 200.

In one embodiment, clinical guidelines describe evidence-based treatment methodologies for particular medical conditions, e.g., information based on medical studies. For instance, evidence-based treatment methodologies are advantageous because they are based on empirical data and have documented success; thus, these treatment methodologies provide greater accountability among health providers, as well as health insurance and other health care related companies. For example, cognitive behavioral therapy is a proven evidence-based treatment methodology for anxiety disorder related medical conditions and is recommended by many therapists and/or medical experts. Following in the same example, the health provider matching service 200 extracts therapist data including a vector of the words "cognitive," "behavioral," and "therapy" (e.g., from terms and/or key terms in a semantic relationship graph) and applies the clinical guidelines to the therapist data to derive quality information, i.e., the health provider matching service 200 analyzes the therapist data in context of the clinical guidelines. In particular, since the clinical guidelines indicate that cognitive therapy is an advantageous medical treatment, the derived quality information indicates that a provider associated with the therapist data is a high quality provider. In some embodiments, the health provider matching service 200 considers, in addition to medical conditions, conditions such as social issues. Patients may experience social issues such as grief, divorce, aging, adjustment to a new child, loss of employment, and other major life transitions. Social issues do not necessarily require medication type treatments.

In another example, clinical guidelines recommend that pregnant women should avoid taking anti-anxiety drugs because babies can develop a dependency on the drugs used by their mothers. Accordingly, quality information based on the clinical guidelines may describe information indicating that medications are a less preferable treatment (i.e., lower quality) for pregnant women who have anxiety related disorders. The clinical guidelines may also recommend people over the age of 65 avoid taking anti-anxiety drugs because anti-anxiety drug use in elderly patients is often associated with an increase in risk of falls based on medical studies. In some embodiments, the term "therapist" is used to specifically describe behavioral health providers who are not able to prescribe medication, such as clinical psychologists, marriage and family therapists, and licensed clinical social workers. In contrast, in some embodiments, the term "prescriber" is used to specifically describe providers who are able to prescribe medication. In the example previously described, the clinical guidelines may recommend that pregnant women seek treatment from "therapists" in particular instead of "prescribers."

Quality information derived from the application of the clinical guidelines can be combined with machine learning techniques to identify terms that are more frequently used by high quality and/or low quality providers. For example, a high quality provider is a provider who frequently (or strictly) adheres to evidence-based treatment methodologies such as cognitive therapy, when treating patients who have anxiety disorders. The health provider matching service 200 determines the provider's adherence based, e.g., at least in part on the occurrence of words related to cognitive therapy in therapist data associated with the high quality provider. In a different example, a low quality provider is a provider who frequently (or always) prescribes anti-anxiety medication for patients who are pregnant women seeking treatment for anxiety disorders. The health provider matching service 200 determines the provider's prescriptions based, e.g., at least in part on the occurrence of words related to anti-anxiety medication in therapist data associated with the low quality provider. The health provider matching service 200 is further described with reference to FIGS. 2-12.

Therapist Matching Service

Figure 2:
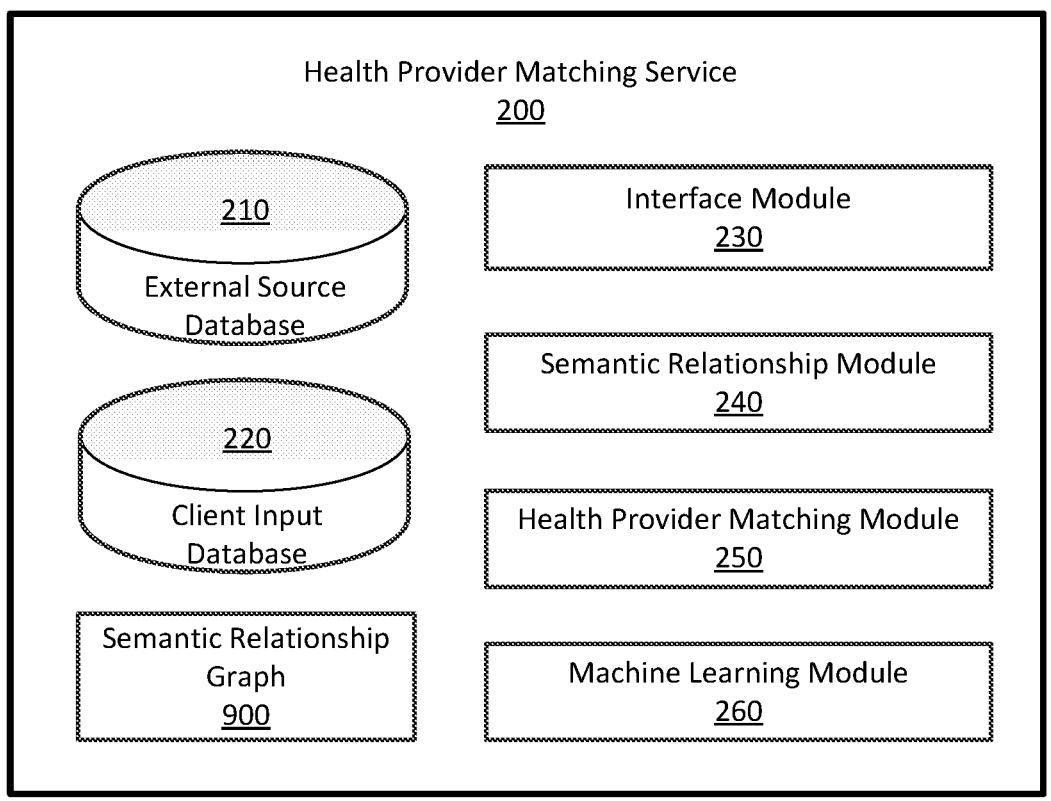
FIG. 2 is a block diagram of the health provider matching service within the computing environment shown in FIG. 1 according to one embodiment.

FIG. 2 is a block diagram of the health provider matching service 200 within the computing environment 100 shown in FIG. 1 according to one embodiment. In the embodiment illustrated in FIG. 2, the health provider matching service 200 has an external source database 210, client input database 220, interface module 230, semantic relationship module 240, health provider matching module 250, machine learning module 260, and semantic relationship graph 900. In alternative configurations, different and/or additional components may be included in the health provider matching service 200. Similarly, functionality of one or more of the components may be distributed among the components in a different manner than is described herein.

The interface module 230 facilitates the communication among the client device 110, the health provider matching service 200, the external source 130, and the health provider source 140. In one embodiment, the interface module 230 interacts with the client devices 110 to receive user input data and stores the received user input data in the client input database 220. Further, the interface module 230 receives information from the external source 130 and/or health provider source 140, and stores the received information in the external source database 210. The interface module 230 can also provide the received information to the health provider matching module 250 and semantic relationship graph 900 (further described in FIG. 9) for further processing. Upon receiving results from the health provider matching module 250, the interface module 230 instructs the software application module 115 of the client device 110 to display the results. In another embodiment, the interface module 230 provides software updates, such as feature updates and security patches, to the software application module 115 of the client device 110 for smooth and secure operation of the software application on the client device 110.

The semantic relationship module 240 identifies semantically related terms that are commonly used by behavioral health therapists and/or patients, e.g., using natural language processing techniques to analyze health information available from resources targeted at health care professionals and educational resources targeted at laypeople. The identified terms are related to different categories of health information including, e.g., the following clusters: conditions, symptoms, medications, therapies, and providers. The semantic relationship module 240 further identifies connections between key terms of the clusters. In one embodiment, the semantic relationship module 240 generates a semantic relationship graph, e.g., the semantic relationship graphs illustrated in FIG. 9 and FIG. 10, to describe the semantic relations among the semantically related terms and connections between key terms. The semantic relationship module 240 is further described with reference to FIG. 3B through FIG. 10.

Figure 9:
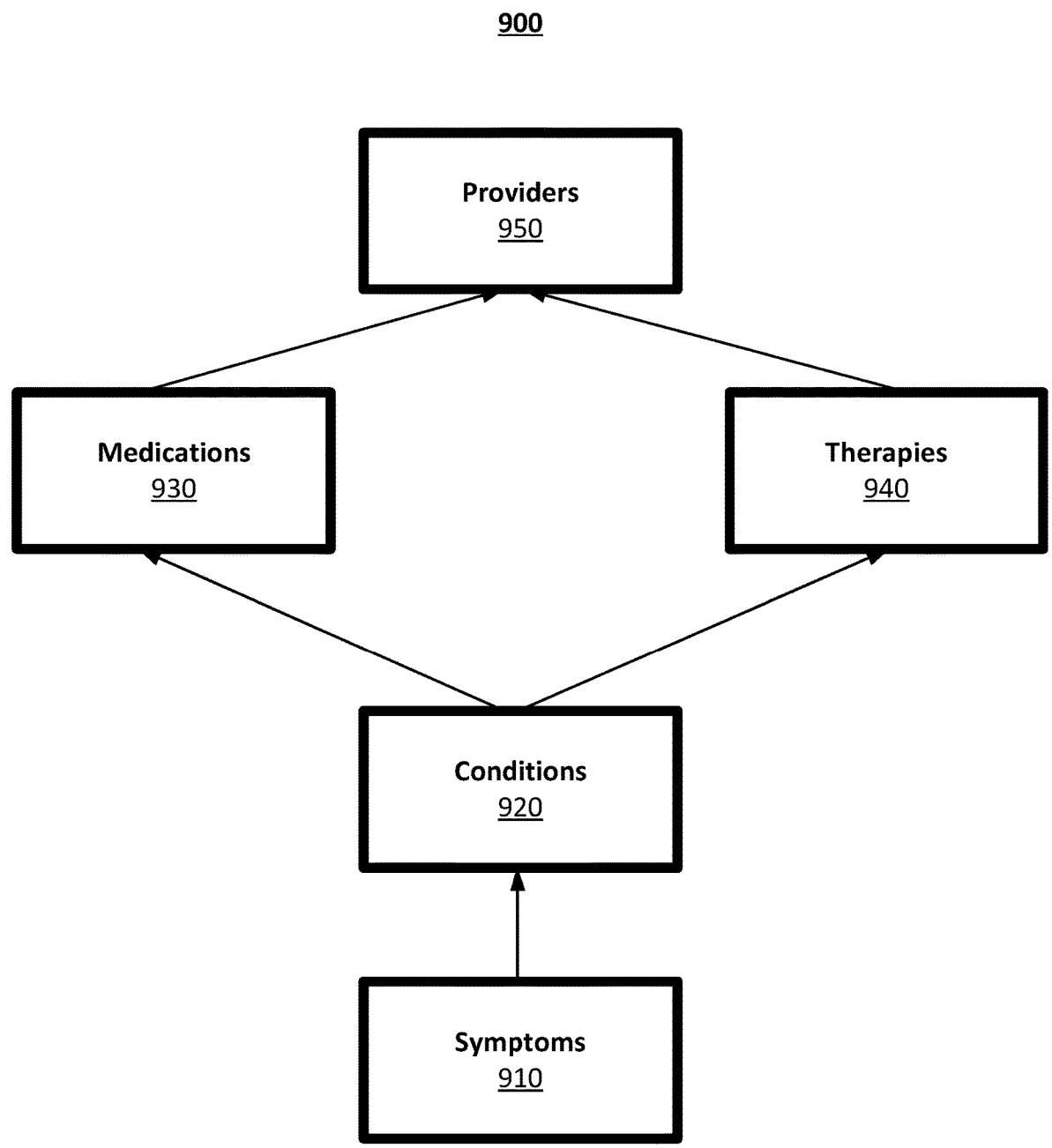
FIG. 9 is a flow diagram illustrating an example semantic relationship graph that links providers to the condition and symptom terms relevant to a patient according to one embodiment.
Figure 10:
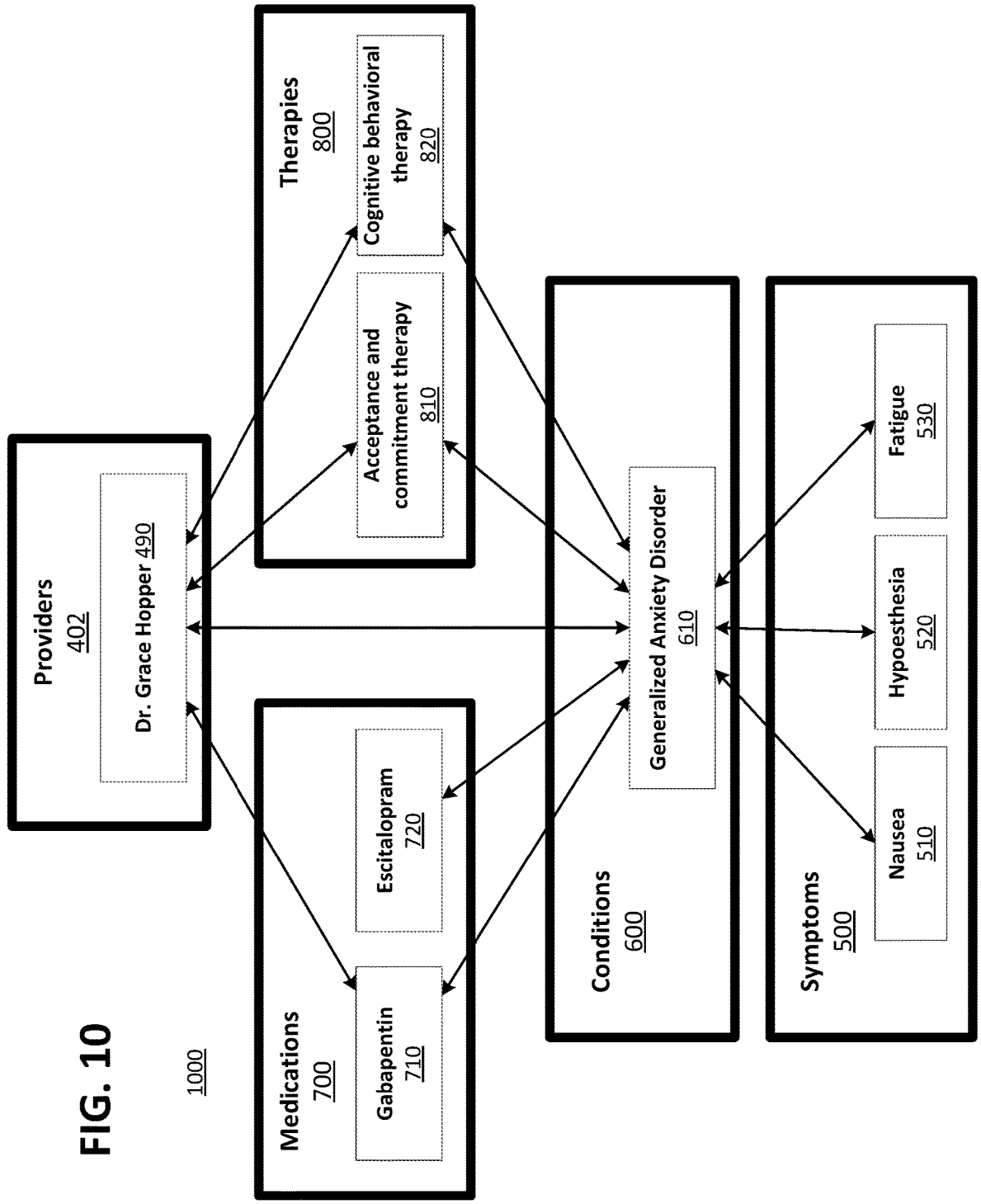
FIG. 10 is a diagram illustrating a semantic relationship graph generated by the health provider matching service showing relationships among key terms associated with example medical condition generalized anxiety disorder, and example medications and therapies offered by Dr. Grace Hopper according to one embodiment.

The health provider matching module 250 generates referrals associated with best matched therapists for a patient based on semantically related medical terms and connected key terms identified by a semantic relationship graph, e.g., semantic relationship graph 900 shown in FIG. 9 and the semantic relationship graph 1000 shown in FIG. 10, which is generated by the semantic relationship module 240. In one embodiment, the health provider matching module 250 calculates a match score indicating the strength of a match between the patient and each therapist of the cluster of providers described in the semantic relationship graph based on the connections between key terms of clusters, i.e., providers, medications, therapies, conditions, and symptoms, described in the semantic relationship graph. For example, the health provider matching module 250 extracts a vector representation of therapist data, e.g., a word vector representation of semantically related terms based on the information provided by the semantic relationship graph 1000 in FIG. 10. The health provider matching module 250 applies one or more clinical guidelines and/or best practices to the therapist data to derive quality information of therapists, e.g., by determining adherence of the therapists to evidence-based methodology for a particular medical condition relevant to the patient.

The health provider matching module 250 can provide a list of matched therapists as the referrals to the patient. In one embodiment, the list includes zero or more therapists whose corresponding match score is above a predefined threshold value. If there are no therapists whose match score is above the threshold value, the health provider matching service 200 can instruct the user via the client device 110 to provide additional information describing the patient and/or the patient's medical needs to help identify a matched therapist. Upon receiving the additional information, the health provider matching module 250 recalculates the match scores for each therapist in the graph 900. The list of the matched therapists includes information associated with each matched therapist, e.g., contact information, location, gender, new patient availability, related medical conditions and treatments that the provider handles, language, education, work experience, and other suitable information related to the matched therapists. In some embodiments, the health provider matching module 250 also generates instructions on how to present the referrals, and provides the presentation instructions associated with referrals to the client device 110 for display to the user.

The machine learning module 260 applies machine learning techniques to the derived quality data of therapists to identify terms and/or key terms that are more frequently used by high quality and/or low quality) providers. The machine learning module 260 provides the identified terms and/or key terms to the health provider matching module 250 to recalculate the matching scores for each therapist in the semantic relationship graph to provide additional differentiation when ranking the therapists. For example, the frequently used terms and/or key terms can be further divided into two sub-groups: terms and/or key terms frequently used by providers known to provide high quality therapy services and terms and/or key terms frequently used by providers known to provide low quality therapy service.

In one embodiment, the machine learning module 260 has one or more databases of frequently used terms and/or key terms describing symptoms, therapies, medications, and conditions. The databases of frequently used terms can be generated using any combination of manual user input into the health provider matching service 200 and machine learning techniques known to one skilled in the art. An expert such as an experienced therapist or physician may provide the manual user input. The databases can be expanded over time by user input, the machine learning module 260, and/or other machine learning techniques. The machine learning module 260 is further described with reference to FIG. 11, which shows an example illustrating frequencies of terms generated by the machine learning module 260, where the terms and their corresponding frequencies used by high quality therapists for treating medication condition of generalized anxiety disorder.

Identifying Semantically Related Medical Terms

The semantic relationship module 240 identifies semantically related terms that are commonly used by behavioral health providers and patients, e.g., using natural language processing techniques to analyze health information available from resources targeted at health care professionals and educational resources targeted at laypeople. The identified terms are related to different categories of health information, including, e.g., the following clusters: conditions, symptoms, medication, therapies, and providers.

Figures 3A, 3B:
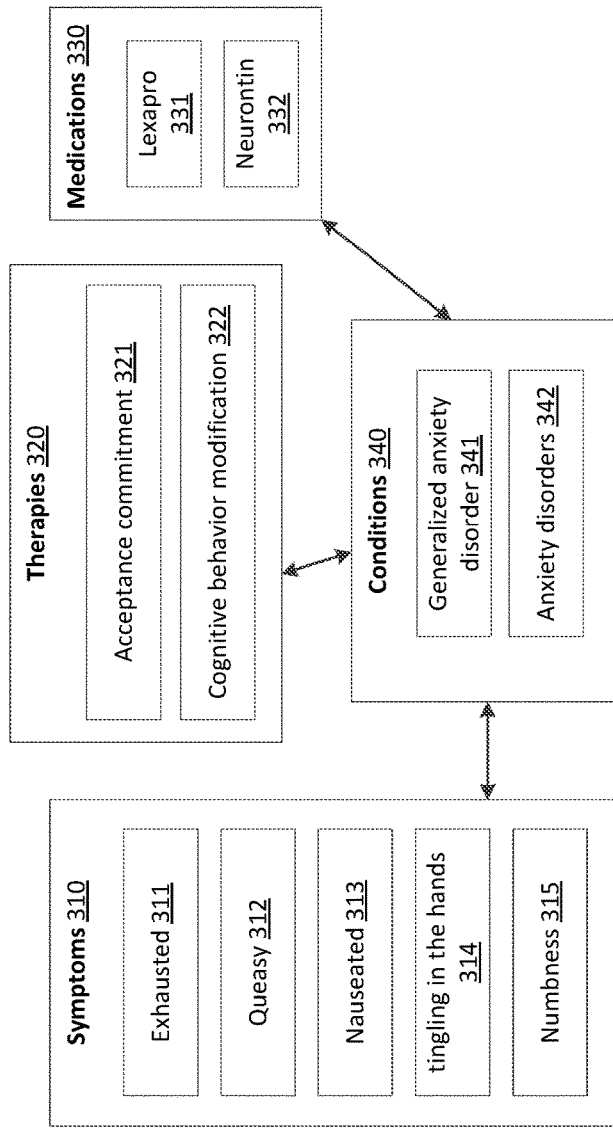
FIG. 3A is a sample of text describing medical terms used by the health provider matching service according to one embodiment.
FIG. 3B is a diagram of terms identified from the sample of text shown in FIG. 3A and organized by the health provider matching service according to one embodiment.

Turning now to FIG. 3A, FIG. 3A is a sample of text 300 describing medical terms used by the semantic relationship module 240 to identify semantically related terms associated with a medical condition called "generalized anxiety disorder" according to one embodiment. In the embodiment illustrated in FIG. 3A, the sample text 300 is retrieved from an external source 130 and parsed by the semantic relationship module 240 of the health provider matching service 200. In this example, the sample text describes information associated with a medical condition called "generalized anxiety disorder" such as symptoms, therapies, and medications. Line numbers next to the sample text 300 in FIG. 3A are for illustration purposes.

FIG. 3B is a diagram of terms identified from the sample of text 300 shown in FIG. 3A and organized by the semantic relationship module 240 of the health provider matching service 200 according to one embodiment. In the embodiment illustrated in FIG. 3B, the semantic relationship module 240 identifies terms in the sample of text 300 and categorizes the identified terms into discrete groups based on the relevance of the terms in a health care context. In one embodiment, the semantic relationship module 240 uses natural language processing techniques, e.g., vector space modeling, to parse the sample of text 300 and to identify relevant terms based on the parsing. The terms are categorized under one of a plurality of clusters, i.e., symptoms 310, therapies 320, medications 330, and conditions 340. For example, terms such as exhausted 311, queasy 312, nauseated 313, tingling in the hands 314, and numbness 315 are categorized as symptoms 310 because these terms each describe a type of symptom; terms such as acceptance commitment 321 and cognitive behavior modification 322 are categorized as therapies 320 because these terms each describe a type of therapy; terms such as Lexapro 331 and Neurontin 332 are categorized as medications 330 because these terms each describe a type of medication; and terms such as generalized anxiety disorder 341 and anxiety disorders 342 are categorized as conditions 340 because these terms each describe a type of condition. Since all of the terms in FIG. 3B were identified from the same sample of text 300, the symptoms 310, therapies 320, and medications 330, are each connected with the conditions 340, as illustrated by the arrows.

In one embodiment, the semantic relationship module 240 has databases of frequently used terms describing symptoms, therapies, medications, and conditions, which are used to categorize terms from the sample of text 300. The databases of frequently used terms can be generated using any combination of manual user input into the health provider matching service 200 and natural language processing techniques known to those skilled in the art. An expert such as an experienced therapist or physician can provide the manual user input. The databases can be expanded over time by user input, the semantic relationship module 240, and/or other natural language processing techniques.

Figure 4A:
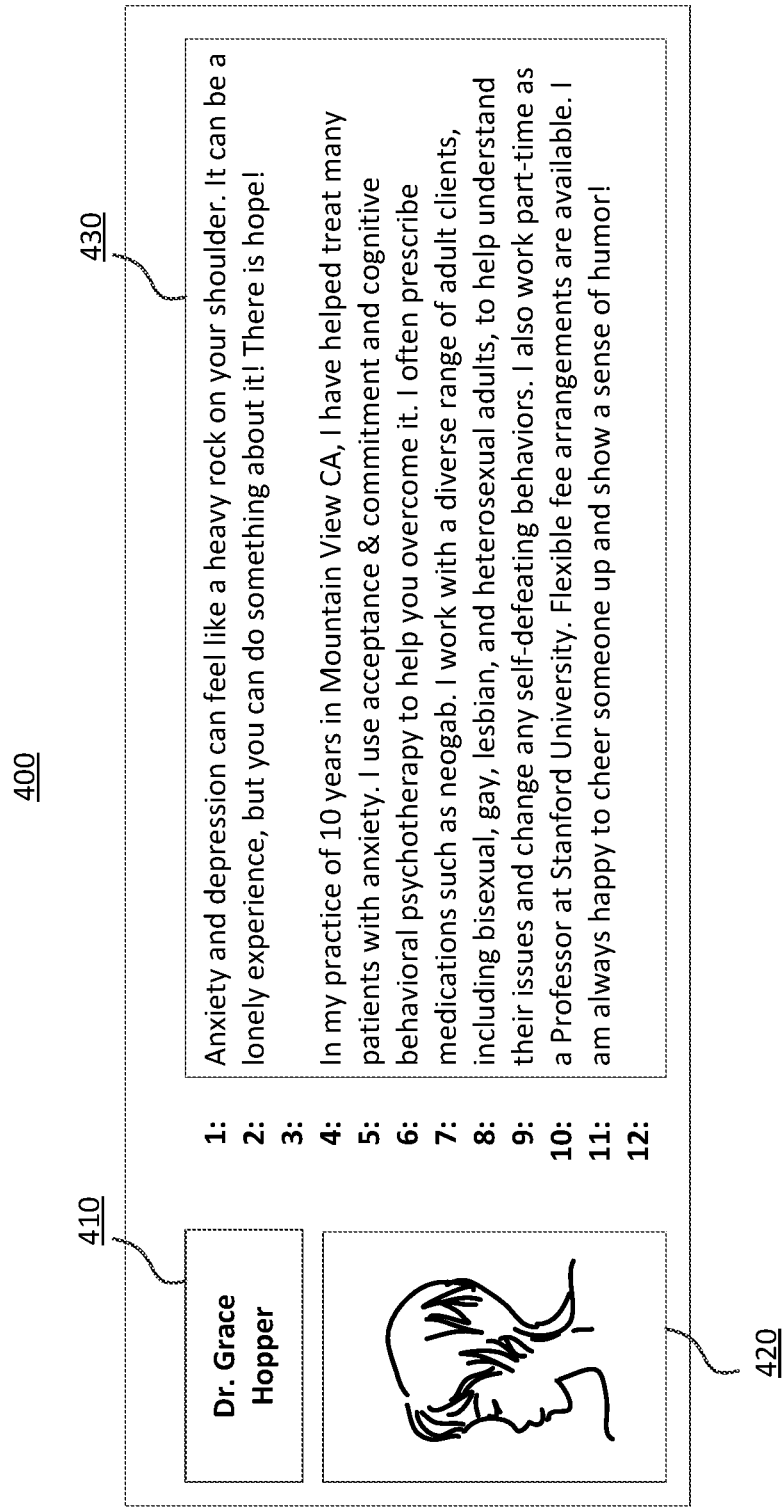
FIG. 4A is an example personal statement by a health provider on her practice website, which is analyzed by the health provider matching service according to one embodiment.

FIG. 4A is an example personal statement 430 by a health care provider on her practice website 400 used by the semantic relationship module 240 to identify terms describing providers according to one embodiment. In the embodiment illustrated in FIG. 4A, the health care provider website 400 also has a therapist name 410 (e.g., Dr. Grace Hopper) and photo 420. The example personal statement 430, therapist name 410, and photo 420 are retrieved and parsed by the semantic relationship module 240 of the health provider matching service 200 from a health provider source 140. In this example, the example personal statement 430 describes information associated with a therapist such as the therapists' experience, conditions treated, offered therapies and medications, and target patients. Line numbers next to the example personal statement 430 in FIG. 4A are for illustration purposes.

Figure 4B:
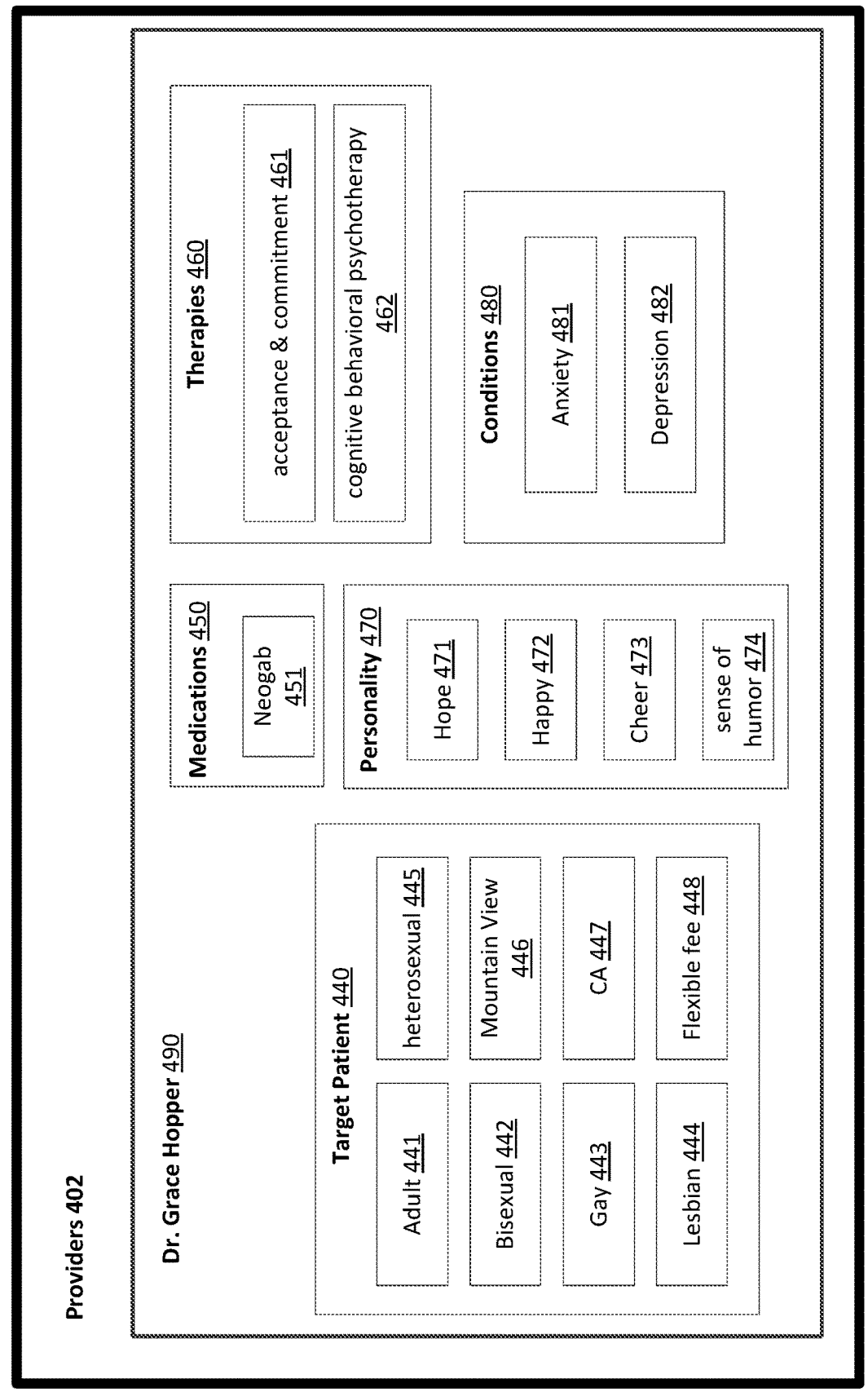
FIG. 4B is a diagram of terms identified from the example personal statement shown in FIG. 4A and organized by the health provider matching service according to one embodiment.

FIG. 4B is a diagram of terms identified from the example personal statement 430 shown in FIG. 4A and organized by the semantic relationship module 240 of the health provider matching service 200 according to one embodiment. In the embodiment illustrated in FIG. 4B, the semantic relationship module 240 identifies terms from the example personal statement 430 and categorizes the identified terms into discrete groups based on the relevance of the terms to one of a plurality of clusters in a health care context. For example, terms such as adult 441, bisexual 442, gay 443, lesbian 444, heterosexual 445, Mountain View 446, CA 447, and flexible fee 448 are categorized as describing a therapist's target patient 440; term neogab 451 is categorized as medications 450; terms such as acceptance & commitment 461 and cognitive behavioral psychotherapy 462 are categorized as therapies 460; terms such as hope 471, happy 472, cheer 473, and sense of humor 474 are categorized as personality 470; and terms such as anxiety 481 and depression 482 are categorized as conditions 480. The target patient 440, medications 450, therapies 460, personality 470, and conditions 480 are connected with the therapist key term, Dr. Grace Hopper 490, which is the therapist name 410 parsed from the health care provider website 400 illustrated in FIG. 4A. Dr. Grace Hopper 490 is associated with a cluster of providers 402. In one embodiment, the semantic relationship module 240 has databases of frequently used terms describing target clients, medications, therapies, personalities, and conditions, which are used to categorize terms from the example personal statement 430.

Therapeutic relationships or therapeutic alliances benefit from personality compatibilities between patients and therapists. Patients have different preferences toward the personality and therapy style of their therapists. For example, a patient prefers a therapist who is typically described as warm and friendly. Another patient prefers a therapist who is more clinical and projects an aura of professional expertise working as a therapist. Yet another patient prefers a therapist who focuses on problem solving. Other personalities and therapy styles include a focus on creating a safe environment, a focus on evidence or research based therapies, and a focus on nurturing personal growth for the patient.

The health provider matching module 250 uses personality-related terms to match patients with providers. The health provider matching module 250 receives input from a patient via the client device 110 (or from the client input database 220) indicating the patient's preferences regarding the provider's personality or style. The health provider matching module 250 uses topic modeling to generate a 2-layer probability distribution to analyze personality or therapy style related words. The first probability distribution determines the probability of a topic appearing in a document. For example, if the document includes multiple instances of the words "therapist" and "personality," then the document is likely to describe the topic of a therapist's personality. Other words that may also indicate a high probability of the topic of a therapist's personality include "warm," "friendly," "clinical," and "professional," among others. The health provider matching module 250 may form clusters of related personality words. For instance, "warm" and "friendly" refer to a similar therapist personality, and thus the two words are clustered together.

The second probability distribution generated by the health provider matching module 250 determines the probability of a word appearing in a document about a topic. For example, if the topic of a document is identified as therapist styles, then words that are likely to appear in the document include "problem solving," "personal growth", and "safe environment," among others. Due to the variety of data sources (e.g., from external sources 130 and health provider sources 140), the health provider matching module 250 takes advantage of both probability distributions to match the patient with therapists that suit the patient's indicated personality and/or style preferences. For example, if a document includes unstructured data, the health provider matching module 250 uses the first probability distribution to identify the topic of the document. If a document includes structured data, for example, the document is a well-known website including personality profiles of therapists, then the health provider matching module 250 uses the second probability distribution to determine which words appearing in the document are likely to be relevant to a therapist's personality.

Semantic Relationship Graph

The semantic relationship module 240 further identifies semantic relations among conditions, symptoms, medication, therapies, and providers. In one embodiment, the semantic relationship module 240 identifies clusters of terms semantically related to key terms of medical conditions, symptoms, medications, and therapies, and generates a semantic relationship graph, e.g., the semantic relationship graphs illustrated in FIG. 9 and FIG. 10, to describe the semantic relations among the semantically related terms. The semantic relationship module 240 uses a variety of natural language processing techniques to determine the semantic relations between words (e.g., terms and key terms). The natural language processing techniques include generating synonym sets, stemming, fuzzy matching, anaphora resolution, weighting based on data source types, and information retrieval techniques, each of which is further described below in this section with reference to FIGS. 5-10. In some embodiments, a user such as a physician validates the semantic relations determined by the semantic relationship module 240.

Figure 5:
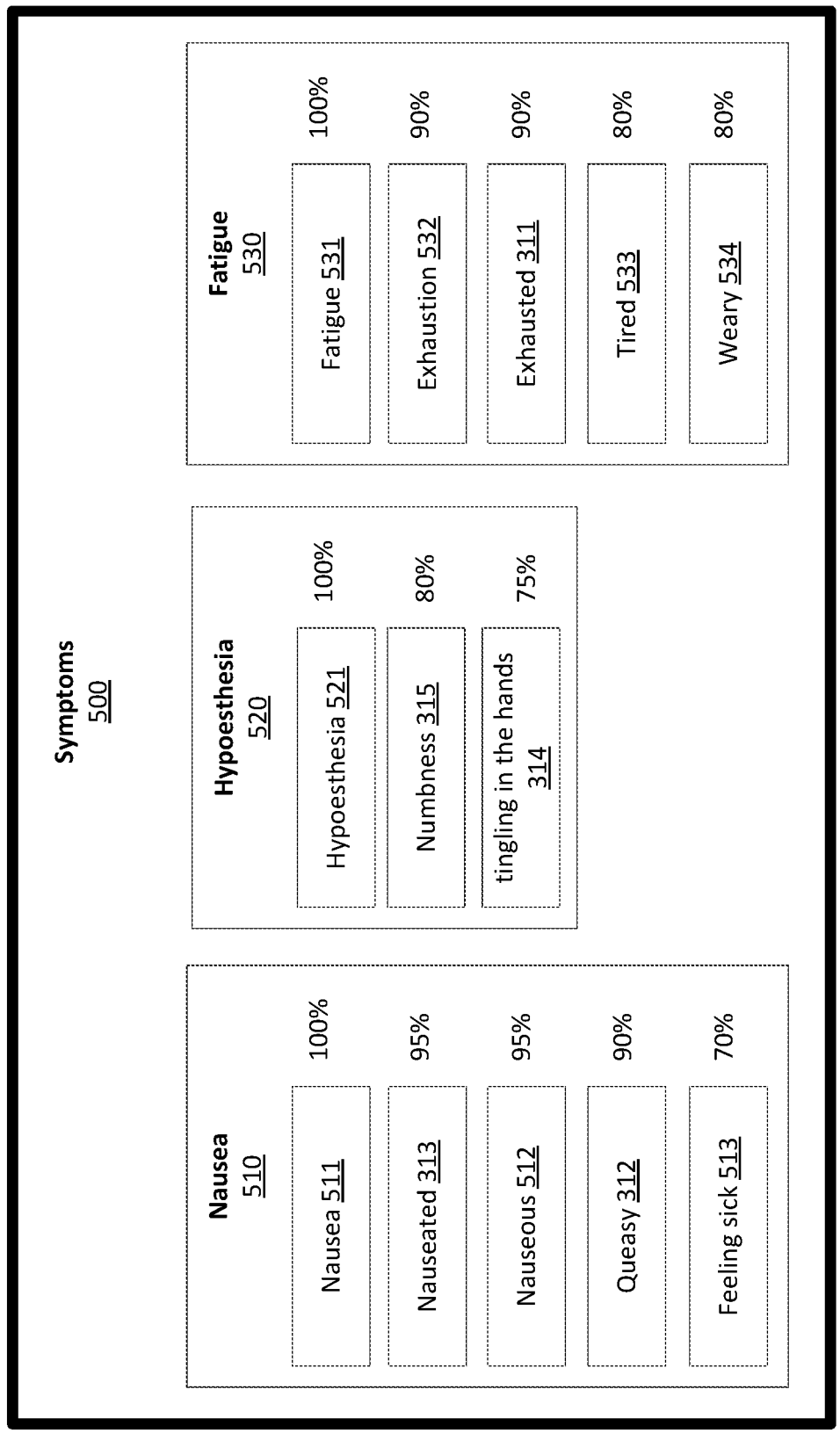
FIG. 5 is a diagram of key terms associated with a cluster of example medical symptoms organized by the health provider matching service according to one embodiment.

FIG. 5 is a diagram of key terms associated with a cluster of example medical symptoms 500 organized by the semantic relationship module 240 according to one embodiment. In the embodiment illustrated in FIG. 5, terms are categorized by the semantic relationship module 240 into discrete groups based on the relevance of the terms to the key terms describing symptoms, nausea 510, hypoesthesia 520, and fatigue 530; each symptom is an element of the cluster of symptoms 500, which is described in a semantic relationship graph, e.g., semantic relationship graph 1000 shown in FIG. 10. For example, terms such as nausea 511, nauseated 313, nauseous 512, queasy 312, and feeling sick 513 are categorized with key term nausea 510. The categorized terms are retrieved from health provider sources 140 (e.g. the health care provider website 400 in FIG. 4), external sources 130 (e.g. the sample of text 300 in FIG. 3), and/or the client device 110.

The semantic relationship module 240 calculates a closeness score, also referred to as score herein, for each term based on its closeness to the key terms of the symptoms 500. For instance, the term nausea 511 has a score of 100% in the nausea 510 group because the term nausea 511 has the exact same characters in the same order as the key term nausea 510. Following in the same example, the term nauseated 313 has a score of 95% because the word nauseated 313 is the verb form of the word nausea. Term nauseated 313 is close to nausea, in terms of having common characters and order of characters, but not exactly the same, so its corresponding score is slightly lower than that of nausea 511. As the terms become less relevant to the symptoms 500, their corresponding scores become lower. The semantic relationship module 240 uses fuzzy matching along with the calculated score. Fuzzy matching connects words that are not are 100% match based on the score. For example, even though nauseated 313 has a score of 95%, which is not quite 100%, nauseated 313 is categorized (connected) under nausea 510. In some embodiments, the semantic relationship module 240 uses fuzzy matching algorithms such as n-grams. For example, the semantic relationship module 240 divides the term nauseated 313 into five elements, "nau," "aus," "sea," "eat," "ted," based on phonetics. Similarly, nausea 510 is divided into three elements, "nau," "aus," "sea." Since nauseated 313 and nausea 510 have three elements in common, the n-gram algorithm determines that there is a high likelihood that nauseated 313 is related to nausea 510. Accordingly, the semantic relationship module 240 calculates a higher closeness score for nauseated 313, relative to a term that has fewer elements in common, e.g., queasy 312. In some embodiments, the semantic relationship module 240 connects words that have a closeness score greater than a threshold value, or a number of common elements (for the n-gram algorithm) greater than a threshold number.

In one embodiment, the semantic relationship module 240 has databases of synonyms, which are used to calculate the scores in FIG. 5. The databases of synonyms can be generated using any combination of manual user input into the health provider matching service 200 and natural language processing techniques. In one embodiment, the natural language processing techniques uses linguistic rules such as stemming to determine the scores. For example, in the English language, the verb form of a word (e.g., nauseated) often ends with the letters "ed", while the adjective form of the word (e.g., nauseous) often ends with the letters "ous". With this information, the semantic relationship module 240 creates a rule that scores a term with a higher score if the difference between the term and the corresponding key term is a difference between the last few letters, i.e., a word "stem," or is a difference between the verb and adjective form (or any other part of speech in a language such as English) of the corresponding key term. The semantic relationship module 240 also uses stemming to generate the database of synonyms, and thus helps determine semantic relationships.

In the embodiment illustrated in FIG. 5, terms such as hypoesthesia 521, numbness 315, and tingling in the hands 314 are categorized with the symptom key term hypoesthesia 520. Terms such as fatigue 531, exhaustion 532, exhausted 311, tired 533, and weary 534 are categorized with the symptom key term fatigue 530. The terms categorized with key term hypoesthesia 520 and key term fatigue 530 have scores determined in a similar method to those determined for the terms categorized with key term nausea 510. The key terms of the symptoms 500, nausea 510, hypoesthesia 520, and fatigue 530, are stored as objects in the semantic relationship graph along with connections to their associated terms and determined scores.

In some embodiments, the semantic relationship module 240 uses information retrieval techniques such as determining a term frequency-inverse document frequency (TF-IDF) for a word or phrase in a data source. Generally, a term that occurs more frequently in a data source is more relevant to the topic of the data source. For example, if a data source includes ten occurrences of the term "symptom" and one occurrence of the term "cow," then the data source is more likely relevant to symptoms of a condition, rather than to cows. However, words including conjunctions such as "and", "but", and "or," as well as antecedents such as "a" and "the" typically occur frequently in data sources regardless of the topic. To account for these types of words, a TF-IDF technique considers the occurrence of these words in a large collection of data sources. For instance, the collection includes documents about a wide variety of health and wellness topics. On average, each document in the collection includes 50 occurrences of the word "and," and one occurrence of the word "symptom." Thus, if a certain document included 40 occurrences of the word "and," and ten occurrences of the word "symptom," then the word "symptom" would likely more indicative of the topic of the document, even though the word "and" occurs more frequently. Specifically, 40 occurrences of "and" is less than the collection average of 50 occurrences, while ten occurrences of "symptom" is greater than the collection average of one occurrence.

Based on the determined TF-IDF for words in a data source, the semantic relationship module 240 identifies terms that are likely to be relevant to a target topic. For example, referring to back FIG. 3A, the sample of text 300 (e.g., a data source) describing medical terms about the topic of anxiety includes the sentence "Physical symptoms such as tingling in the hands or numbness." In a collection of data sources, the word "tingling" occurs on average 0.1 times per document of the collection. Further, the word "tingling" occurs on average 0.01 times per document when the document also includes the word "hands." Thus, the occurrence of both "tingling" and "hands" in the sentence indicates that these two words are likely to be relevant to the topic of symptoms. The semantic relationship module 240 uses TF-IDF along with information about the context of a sentence. For example, the words "tingling" and "hands" is followed by the words "or numbness." Thus, the semantic relationship module 240 determines that "tingling" and "hands" are related to "numbness." Accordingly, the terms tingling in the hands 314 and numbness 315 are categorized together under symptom key term hypoesthesia 520, which is also a synonym of "numbness".

In some embodiments, the semantic relationship module 240 determines TF-IDF for words while considering the length of a document. For instance, the word "therapy" occurs once in a document. The word "therapy" is more likely to be more relevant to the topic of the document's length is 50 words, rather than 500 words. Additionally, in some embodiments, the semantic relationship module 240 uses information retrieval techniques such as a bag of words model or bag of words retrieval function (e.g., Okapi "Best Matching" BM25). In particular, the bag of words includes specific words that the semantic relationship module 240 searches for, or weighs more heavily relative to other words, when parsing words from data sources to determine TF-IDF. An expert such as a data scientist may provide target words to train the bag of words model.

Figure 6:
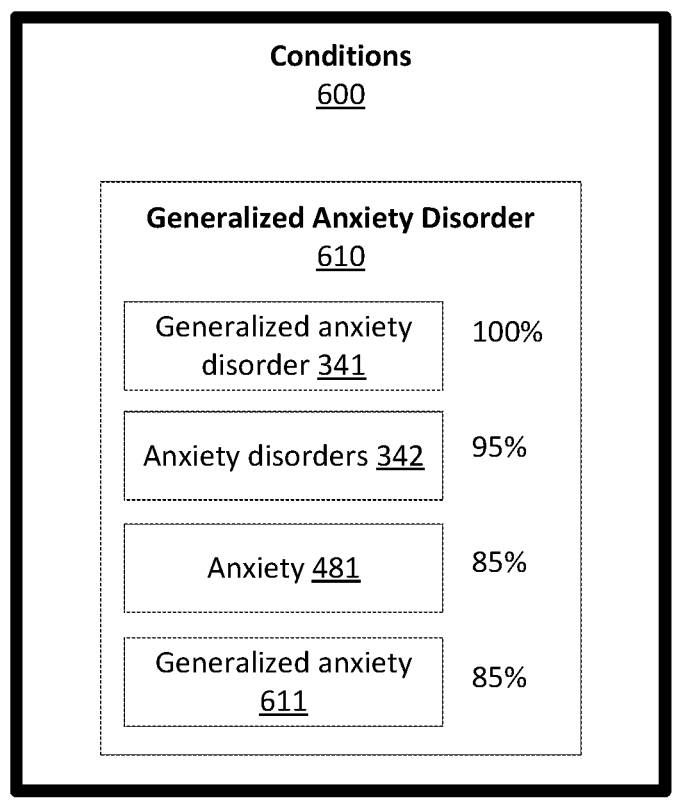
FIG. 6 is a diagram of key terms associated with a cluster of example medical conditions organized by the health provider matching service according to one embodiment.

FIG. 6 is a diagram of key terms associated with a cluster of example medical conditions 600 organized by the semantic relationship module 240 according to one embodiment. In the embodiment illustrated in FIG. 6, terms are categorized by the semantic relationship module 240 into discrete groups based on the relevance of the terms to the key term general anxiety disorder 610, which is an example of a condition, and thus associated with the cluster of conditions 600 as an element of the cluster of conditions 600. For example, terms such as general anxiety disorder 341, anxiety disorder 342, anxiety 481, and generalized anxiety 611 are categorized with key term general anxiety disorder 610. The categorized terms are retrieved from health provider sources 140 (e.g. the health care provider website 400 in FIG. 4), external sources 130 (e.g. the sample of text 300 in FIG. 3), and the client device 110.

The semantic relationship module 240 calculates a score for each term based on its closeness to key terms of the conditions 600. For instance, the term general anxiety disorder 341 has a score of 100% in the key term general anxiety disorder 610 group because the term general anxiety disorder 341 has the exact same characters in the same order as the key term general anxiety disorder 610. Following in the same example, the term anxiety disorders 342 has a score of 95% because the term anxiety disorders 342 is close to the key term, general anxiety disorder 610, in terms of having common characters and order of characters, but not exactly the same, so its corresponding score is slightly lower than that of general anxiety disorder 341. As the terms become less relevant to the key term in the conditions 600, their corresponding scores become lower.

The terms categorized with key term general anxiety disorder 610 have scores determined in a similar method to those determined for the terms categorized with key term nausea 510 as described in FIG. 5. The key terms of conditions 600 such as general anxiety disorder 610 are stored as objects in a semantic relationship graph, e.g., semantic relationship graph 1000 shown in FIG. 10, along with connections to their associated terms and determined scores.

FIG. 7 is a diagram of key terms associated with a cluster of example medications 700 organized by the semantic relationship module 240 according to one embodiment. In the embodiment illustrated in FIG. 7, the terms are categorized by the semantic relationship module 240 into discrete groups based on the relevance of the terms to the key terms, gabapentin 710 and escitalopram 720, which describe examples of medications, and thus are associated with the cluster of medications 700. For example, terms such as gabapentin 711, neogab 451, and Neurontin 332, are categorized with key term gabapentin 710. The categorized terms are retrieved from health provider sources 140 (e.g. the health care provider website 400 in FIG. 4), external sources 130 (e.g. the sample of text 300 in FIG. 3), and the client device 110.

The semantic relationship module 240 calculates a score for each term based on its closeness to the key terms of the medications 700. For instance, the term gabapentin 711 has a score of 100% in the key term gabapentin 710 group because the term gabapentin 711 has the exact same characters in the same order as the key term gabapentin 710. Following in the same example, the term Neurontin 451 has a score of 80% because the medication key term gabapentin 710 (e.g., a generic name) is marketed under the brand name Neurontin 451. The semantic relationship module 240 considers brand names and generic names as synonyms in the context of types of medications. The term Neurontin 451 is relevant to key term gabapentin 710, but Neurontin 451 has a lower corresponding score than that of gabapentin 711 because the term Neurontin 451 has different characters than the key term gabapentin 710. As the terms become less relevant to the key term in the medications 700, their corresponding scores become lower.

In the embodiment illustrated in FIG. 7, terms such as escitalopram 721, escitalopram oxalate 722, and Lexapro 331 are categorized with the medication key term escitalopram 720. The terms categorized with key term escitalopram 720 have scores determined in a similar method to those determined for the terms categorized with key term nausea 510 as described in FIG. 5. The key terms of the medications 700, gabapentin 710 and escitalopram 720, are stored as objects in the semantic relationship graph, e.g., semantic relationship graph 1000 shown in FIG. 10, along with connections to their associated terms and determined scores.

Figure 8:
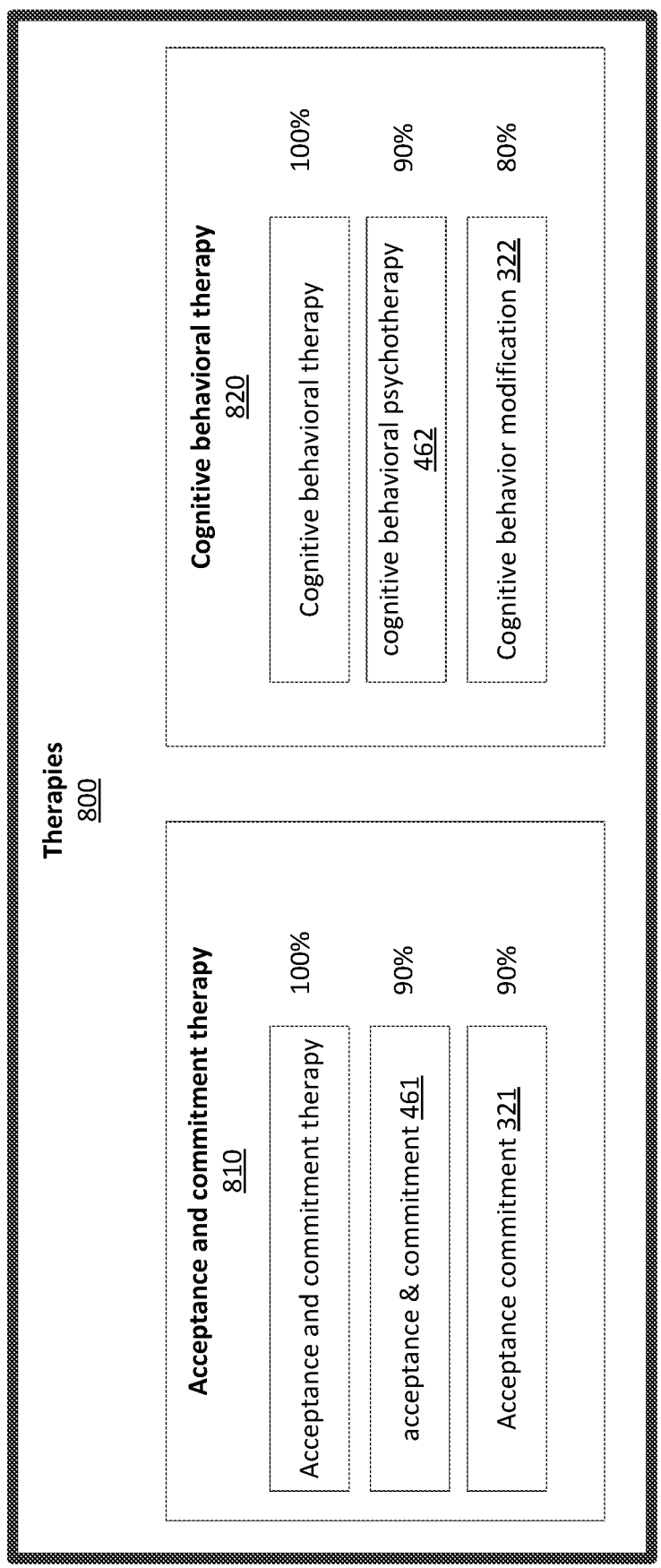
FIG. 8 is a diagram of key terms associated with a cluster of example medical therapies organized by the health provider matching according to one embodiment.

FIG. 8 is a diagram of key terms associated with a cluster of example medical therapies 800 organized by the semantic relationship module 240 according to one embodiment. In the embodiment illustrated in FIG. 8, the terms are categorized by the semantic relationship module 240 into discrete groups based on the relevance of the terms to the key terms, acceptance and commitment therapy 810 and cognitive behavioral therapy 820, which describe discrete examples of therapies, and thus are associated with the cluster therapies 800. For example, terms such as acceptance and commitment therapy 811, acceptance & commitment 461, and acceptance commitment 321 are categorized with key term acceptance and commitment therapy 810. The categorized terms are retrieved from health provider sources 140 (e.g. the health care provider website 400 in FIG. 4), external sources 130 (e.g. the sample of text 300 in FIG. 3), and the client device 110.

The semantic relationship module 240 calculates a score for each term based on its closeness to the key terms of the therapies 800. For instance, the term acceptance and commitment therapy 811 has a score of 100% in the key term acceptance and commitment therapy 810 group because the term acceptance and commitment therapy 811 has the exact same characters in the same order as the key term acceptance and commitment therapy 810. Following in the same example, the term acceptance & commitment 461 has a score of 90% because the term acceptance & commitment 461 is close to the key term, acceptance and commitment therapy 810, in terms of having common characters and order of characters, but not exactly the same, so its corresponding score is slightly lower than that of acceptance and commitment therapy 811. As the terms become less relevant to the therapies 800, their corresponding scores become lower.

In the embodiment illustrated in FIG. 8, terms such as cognitive behavioral therapy 821, cognitive behavioral psychotherapy 462, and cognitive behavioral modification 322 are categorized with the key term, cognitive behavioral therapy 820. The terms categorized with key term cognitive behavioral therapy 820 have scores determined in a similar method to those determined for the terms categorized with key term nausea 510 as described in FIG. 5. The key terms of the therapies 800, acceptance and commitment therapy 810 and cognitive behavioral therapy 820, are stored as objects in the semantic relationship graph 900 along with connections to their associated terms and determined scores. Though the closeness scores illustrated in FIG. 5 through FIG. 8 are percentage values, in other embodiments, the scores determined for each term may be a numerical value or another form of data suitable for ranking the closeness and/or relevance of terms with key terms.

FIG. 9 is a flow diagram illustrating an example semantic relationship graph 900 that connects providers to condition and symptom terms relevant to a patient according to one embodiment. In the embodiment illustrated in FIG. 9, the semantic relationship graph 900 shows connections, represented by arrows, among clusters of key terms, symptoms 910, conditions 920, medications 930, therapies 940, and providers 950. The semantic relationship graph 900 connects the providers 950 to the conditions 920 and symptoms 910 relevant to a patient, e.g., the patient has symptoms described by the terms of the symptoms cluster 910. Using connections between key terms of symptoms 910, conditions 920, medications 930, therapies 940, and providers 950 identified by the semantic relationship module 240, the health provider matching service 200 connects synonyms and interchangeable terms (i.e., semantically related terms) used by laypersons (e.g., the patient) when describing symptoms to therapist data represented by the conditions 920, medications 930, therapies 940, and providers 950 clusters. Based on the information provided by the semantic relationship graph 900, the health provider matching module 250 makes relevant recommendations to the patient even if the search term from the patient's referral request is not present in the therapist data of providers 950.

In one embodiment, the semantic relationship graph 900 is represented by a tree data structure having multiple nodes and edges stored in a computing server of the health provider matching service 200. Each term and key term is represented by a node and each connection is represented by an edge between the two nodes that are connected. Nodes store the value of the term (e.g., the text of the term general anxiety disorder). Nodes of terms are organized into groups categorized under a node of a key term. Further, nodes of key terms are organized into different cluster types (e.g., providers, medications, therapies, conditions, and symptoms); a cluster type may also be represented by a node. In embodiment, there are different types of edges. For example, an edge between a term and a key term stores the closeness score value (e.g., 90%) between the term and the key term. However, an edge that connects two terms categorized under the same key term does not necessarily store a closeness score. Further, an edge connecting a key term node and a cluster type node does not necessarily store a closeness score. In another embodiment, each node of a term stores information indicating which key term and cluster type to which the node is associated.

FIG. 10 is a diagram illustrating a semantic relationship graph 1000 generated by the semantic relationship module 240 showing connections between key terms associated with example medical condition generalized anxiety disorder, and example medication and therapies offered by Dr. Grace Hopper according to one embodiment. The semantic relationship graph 1000 is an embodiment of the semantic relationship graph 900 in FIG. 9.

The semantic relationship graph 1000 includes clusters of providers 402 (illustrated in FIG. 4B), symptoms 500 (illustrated in FIG. 5), conditions 600 (illustrated in FIG. 6), medications 700 (illustrated in FIG. 7), and therapies 800 (illustrated in FIG. 8). Each cluster includes one or more key terms associated with the cluster. For example, key term Dr. Grace Hopper 490 is associated with the providers 402 cluster; key terms such as gabapentin 710 and escitalopram 720 are associated with medications 700 cluster; key terms such as acceptance and commitment therapy 810 and cognitive behavioral therapy 820 are associated with therapies 800 cluster; key term generalized anxiety disorder 610 is associated with conditions 600 cluster; and key terms nausea 510, hypoesthesia 520, and fatigue 530 are associated with symptoms 500 cluster. The terms semantically related to each key term are not shown in FIG. 10 for clarity purposes, but are illustrated in FIG. 4B through FIG. 8 for the providers cluster 402, medications cluster 700, therapies cluster 800, conditions cluster 600, and symptoms cluster 500.

In the embodiment illustrated in FIG. 10, arrows represent connections between key terms generated by the semantic relationship module 240 based on information from the client device 110, external source 130, and/or health provider source 140. For example, Dr. Grace Hopper 490 is connected to the key terms gabapentin 710, acceptance and commitment therapy 810, cognitive behavioral therapy 820, and generalized anxiety disorder 610. The connections have varying strengths based on the scores calculated for each key term. For instance, as shown in FIG. 7, the term neogab 451 has a closeness score of 90% with the key term, gabapentin 710. The term neogab 451 was identified from the provider website 400 shown in FIG. 4A associated with Dr. Grace Hopper 490 as shown in FIG. 4B. Therefore, the strength of the connection between the Dr. Grace Hopper 490 and gabapentin 710 key terms is based on the score of 90%. Similarly, the connection between the Dr. Grace Hopper 490 and acceptance and commitment therapy 810 key terms is based on the score of 90% corresponding to the term acceptance & commitment 461 in FIG. 8 because the term acceptance & commitment 461 is associated with key term Dr. Grace Hopper 490 as shown in FIG. 4B; the connection between the Dr. Grace Hopper 490 and cognitive behavioral therapy 820 key terms is based on the score of 90% corresponding to the term cognitive behavioral psychotherapy 462 in FIG. 8 because cognitive behavioral psychotherapy 462 is associated with key term Dr. Grace Hopper 490 as shown in FIG. 4B; the connection between the Dr. Grace Hopper 490 and general anxiety disorder 610 key terms is based on the score of 85% corresponding to the term anxiety 481 in FIG. 6 because the anxiety 481 is associated with key term Dr. Grace Hopper 490 as shown in FIG. 4B.

In addition to identifying the source of key terms, the semantic relationship module 240 also uses anaphora resolution to determine the connections and/or weighting of connections associated with Dr. Grace Hopper 490. For example, referring back to Dr. Grace Hopper's practice website 400 shown in FIG. 4A, the personal statement 430 includes the sentences: "In my practice of 10 years in Mountain View Calif., I have helped treat many patients with anxiety. I use acceptance & commitment and cognitive behavioral psychotherapy to help you overcome it." In the second sentence, the word "it" is a pronoun that refers to the noun "anxiety" in the first sentence. In this case, "it" is the anaphor, and the semantic relationship module 240 resolves the anaphor by determining that "it" refers to "anxiety." Thus, the semantic relationship module 240 determines that the terms "acceptance & commitment" and "cognitive behavioral psychotherapy" are related to "anxiety" because the former two are used to overcome "it," i.e., "anxiety," based on the second sentence. Further, the semantic relationship module 240 uses anaphora resolution to determine that the words "my" and "I" in the sentences refer to the noun Dr. Grace Hopper 490. Accordingly, in the semantic relationship graph 1000, Dr. Grace Hopper 490 is connected to generalized anxiety disorder 610 (i.e., related to "anxiety") and acceptance and commitment therapy 810 (i.e., related to "acceptance & commitment and cognitive behavioral psychotherapy").

In some embodiments, the semantic relationship module 240 determines weightings of connections in the semantic relationship graph 1000 based on the type of data source. For example, the "Diagnostic and Statistical Manual of Mental Disorders, Fifth Edition" (DSM-5) is a structured data source (e.g., an external source 130) and an authoritative resource for psychiatric diagnosis used by many therapists. On the other hand, Wikipedia® is an unstructured data source which contains information in different formats (e.g., depending on a particular author) as well as links to other websites, some of which may be more credible than others. The semantic relationship module 240 weighs structured data sources such as DSM-5 more heavily than unstructured data sources such as Wikipedia® because the former is more likely to be a reliable and accurate data source.

Following in the same instance in FIG. 10, the term Neurontin 332 has a closeness score of 80% with the key term, gabapentin 710 as shown in FIG. 7. The term Neurontin 332 was identified from the sample of text 300 from the external source 130 described in FIG. 3A. The term generalized anxiety disorder 341 has a closeness score of 100% with the key term, generalized anxiety disorder 610, and the term anxiety disorders 342 has a closeness score of 95% with the key term, generalized anxiety disorder 610, as shown in FIG. 6. The terms, generalized anxiety disorder 341 and anxiety disorders 342, were identified from the sample of text 300 from the external source 130 described in FIG. 3A. Since the medications 330 are connected with the conditions 340 as shown in FIG. 3B, the strength of the connection between the key terms gabapentin 710 and generalized anxiety disorder 610 is based on the scores of 80% (in FIG. 7), 100%, and 95% (in FIG. 6) corresponding to the term Neurontin 332, the term generalized anxiety disorder 341, and the term anxiety disorders 342, respectively.

The strength of the connection may be calculated using a weighted average of the scores (i.e., 80%, 100%, and 95%). The weight applied to each score may be the same or different based on the key term. For instance, the scores of terms categorized under the conditions 600 cluster may be weighed more heavily than the scores of terms categorized under the medications 700 cluster. In another example, the weights may vary based on the number of terms categorized under a key term and/or statistics describing the scores of terms categorized under a key term. For instance, if the standard deviation of scores of terms under a key term is greater in value (relative to the standard deviations of scores of terms under other key terms), the weights applied to each score under the key term when determining strengths of connections in the graph 900 may be decreased because a greater standard deviation may correspond to a weaker prediction of connectivity between terms.

Following in the same instance in FIG. 10, the strength of the connection between the key terms escitalopram 720 and generalized anxiety disorder 610 is based on the scores of 80% (in FIG. 7), 100%, and 95% (in FIG. 6) corresponding to the term Lexapro 331, the term generalized anxiety disorder 341, and the term anxiety disorders 342, respectively. The strength of the connection between the key terms acceptance and commitment therapy 810 and generalized anxiety disorder 610 is based on the scores of 90%, (in FIG. 8) 100%, and 95% (in FIG. 6) corresponding to the term acceptance commitment 321, the term generalized anxiety disorder 341, and the term anxiety disorders 342, respectively. The strength of the connection between the key terms cognitive behavioral therapy 820 and generalized anxiety disorder 610 is based on the scores of 80%, (in FIG. 8) 100%, and 95% (in FIG. 6) corresponding to the term cognitive behavior modification 322, the term generalized anxiety disorder 341, and the term anxiety disorders 342, respectively. The strength of the connection between the key terms nausea 510 and generalized anxiety disorder 610 is based on the scores of 95%, 90% (in FIG. 5), 100%, and 95% (in FIG. 6) corresponding to the term nauseated 313, the term queasy 312, the term generalized anxiety disorder 341, and the term anxiety disorders 342, respectively. The strength of the connection between the key terms hypoesthesia 520 and generalized anxiety disorder 610 is based on the scores of 80%, 75% (in FIG. 5), 100%, and 95% (in FIG. 6) corresponding to the term numbness 315, the term tingling in the hands 314, the term generalized anxiety disorder 341, and the term anxiety disorders 342, respectively. The strength of the connection between the key terms fatigue 530 and generalized anxiety disorder 610 is based on the scores of 90% (in FIG. 5), 100%, and 95% (in FIG. 6) corresponding to the term exhausted 311, the term generalized anxiety disorder 341, and the term anxiety disorders 342, respectively.

In alternate embodiments, the semantic relationship graph 1000 may have different and/or one or more key terms associated with each cluster. For example, another key term under the providers 402 cluster may be "Dr. Sigmund Freud," another key term under the medications 700 cluster may be "aspirin," another key term under the therapies 800 cluster may be "exercise," another key term under the conditions 600 cluster may be "boanthropy," and another key term under the symptoms 500 cluster may be "overeating." Different, greater, and/or fewer connections may exist between any combination of key terms between clusters or within each cluster. Different, greater, or fewer clusters may exist in the graph 1000. As the health provider matching service 200 receives and identifies more terms from samples of text from external sources 130, health provider sources 140, and information from the client device 110, the semantic relationship module 240 has more data from which to use to expand the graph 1000 by generating additional terms, key terms, clusters, and/or connections between key terms. Though the semantic relationship graph 1000 includes one condition, it should be noted that, in practice, semantic relationship graphs can include multiple conditions as well as multiple types of conditions (e.g., medical conditions, social issues, etc.).

Frequency of Terms and Additional Differentiation

Figure 11:
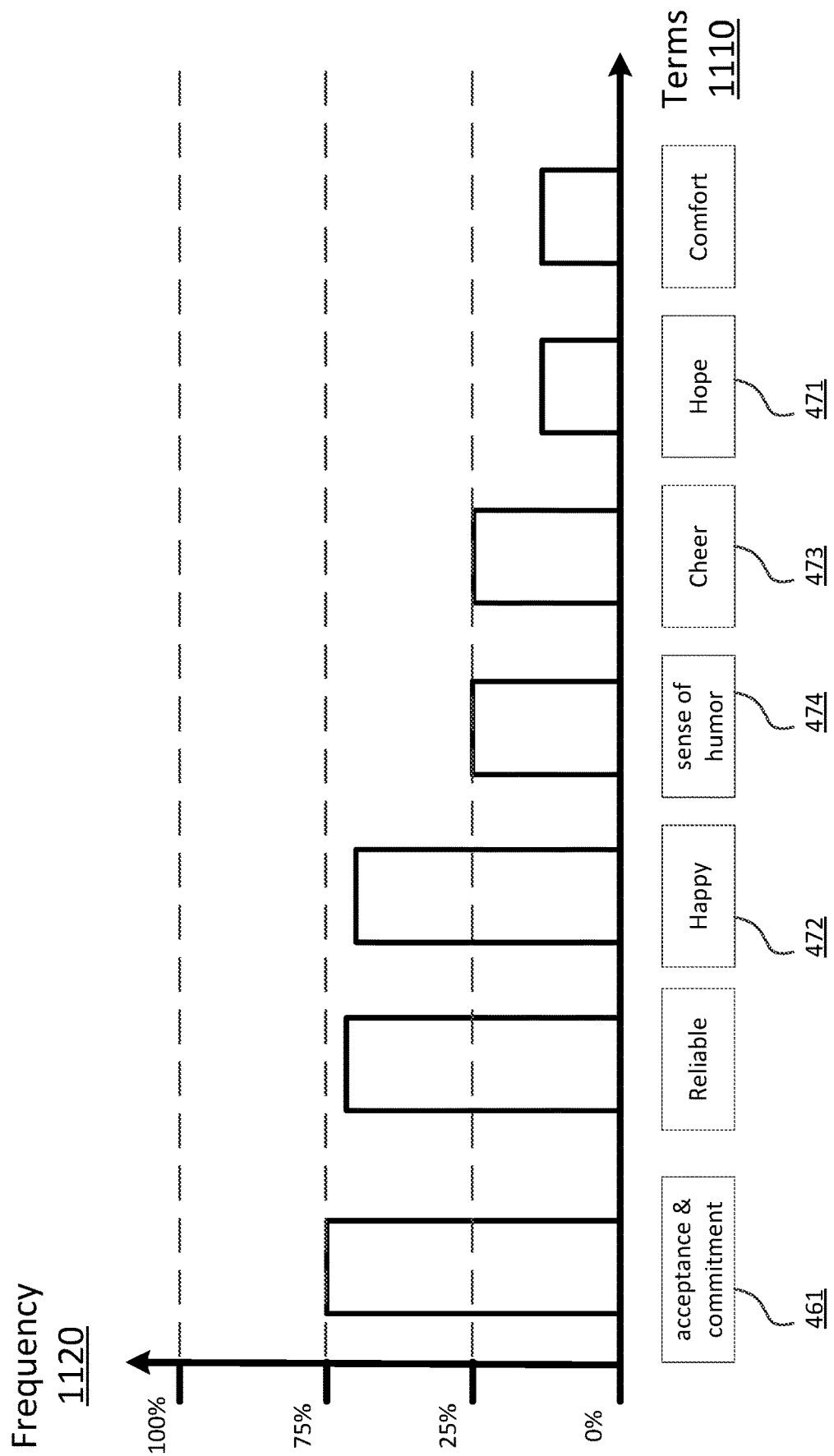
FIG. 11 is a graph illustrating frequencies of terms generated by the health provider matching service according to one embodiment.

FIG. 11 is a graph illustrating frequencies of terms generated by the health provider matching service 200 according to one embodiment. As described above with reference to FIG. 2, the machine learning module 260 applies machine learning techniques to the derived quality data of therapists to identify terms, which are more frequently used by high quality and/or low quality providers. The machine learning module 260 provides the identified terms to the health provider matching module 250 for updating and/or recalculating the matching scores for each therapist (i.e., health care provider) in the graph 900 to provide additional differentiation when ranking the therapists. FIG. 11 shows frequencies of terms generated by the machine learning module 260, where the terms and their corresponding frequencies used by high quality therapists for treating medication condition of generalized anxiety disorder.

In the embodiment illustrated in FIG. 11, the horizontal axis of the bar graph includes the terms 1110 that are most frequently associated and/or connected with high quality therapists in a semantic relationship graph, and the vertical axis of the bar graph represents the corresponding frequencies 1120. The terms in the chart may be identified from information from the client device 110, external source 130, and/or health provider source 140 as shown in FIG. 4B. For example, the term acceptance & commitment 461 is associated and/or connected with 75% of the high quality therapists in the graph 900, while the term cheer 473 is associated and/or connected with 25% of the high quality therapists in the graph 900. A therapist in the semantic relationship graph can be identified as a high quality therapist based on user ratings, patient testimonials, expert evaluations, or other criteria used by the health provider matching service 200. In one embodiment, the health provider matching module 250 uses the bar graph illustrated in FIG. 11 in combination with the semantic relationship graph such as the graph 1000 to identify high quality therapists to be matched to patients. For instance, a match score of a provider will be greater if the provider is connected with terms that are most frequently associated and/or connected with high quality therapists in a semantic graph.

Matching Therapists and Applications

Figure 12:
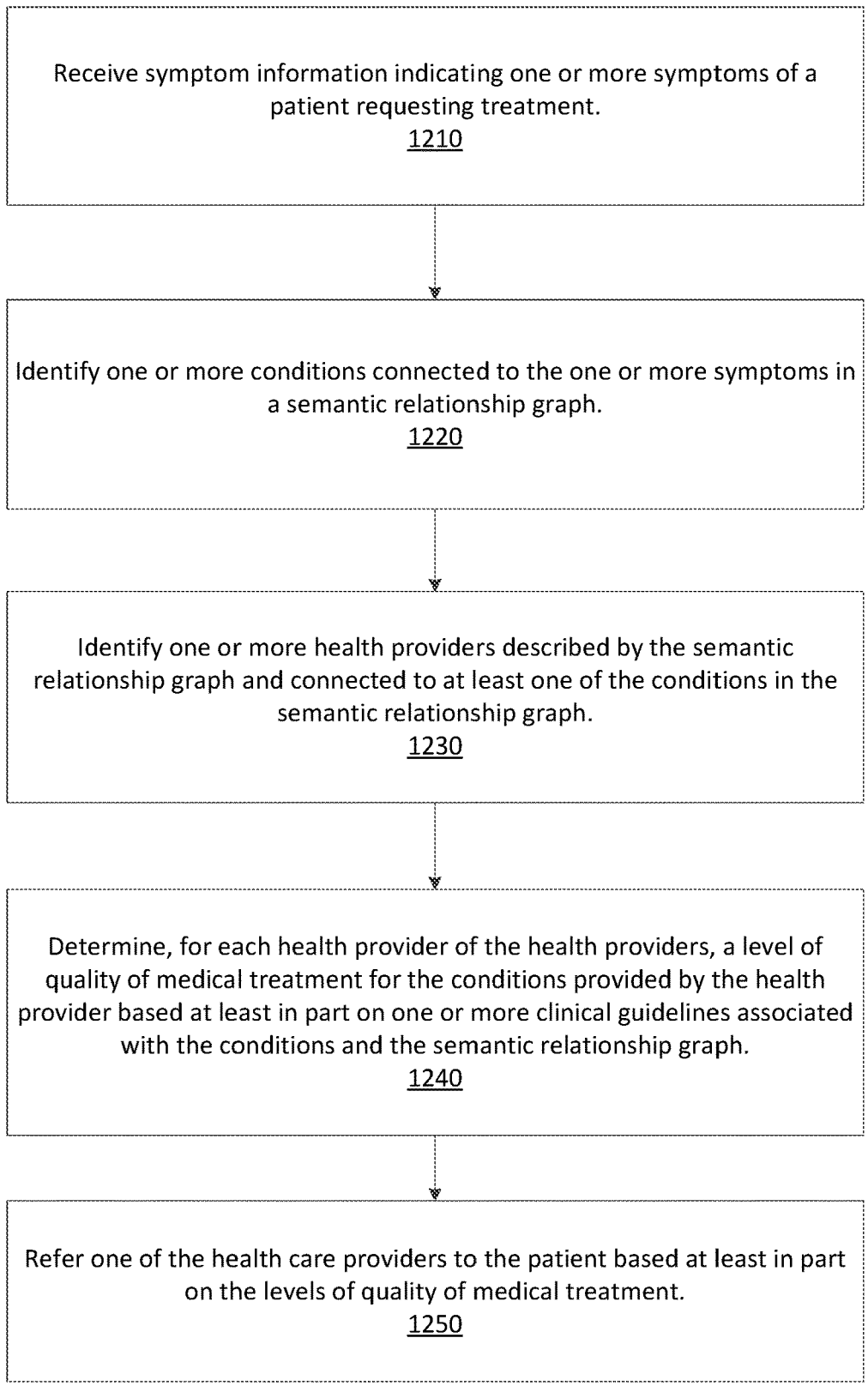
FIG. 12 is a flow chart illustrating a process for matching health providers to patients within the computing environment of FIG. 1 according to one embodiment.

FIG. 12 is a flow chart illustrating a process for matching health providers to patients within the computing environment of FIG. 1 according to one embodiment. The process may include different or additional steps than those described in conjunction with FIG. 12 in some embodiments or perform steps in different orders than the order described in conjunction with FIG. 12.

In the embodiment illustrated in FIG. 12, the health provider matching service 200 receives 1210 symptom information indicating one or more symptoms (e.g., "nausea," "hypothesia", and "fatigue") of a patient requesting treatment, e.g., from a client device 110. The health provider matching service 200 identifies 1220 one or more conditions connected to the one or more symptoms in a semantic relationship graph, e.g., semantic relationship graph 1000 in FIG. 10 including connections between key terms describing at least one of treatments, therapies, medications, symptoms, health care providers, and/or medical conditions. For instance, as shown in FIG. 10, condition, "generalized anxiety disorder" is connected to the one or more symptoms, "nausea," "hypothesia", and "fatigue." The health provider matching service 200 identifies 1230 one or more health providers described by the semantic relationship graph (e.g., semantic relationship graph 1000 in FIG. 10) and connected to at least one of the conditions in the semantic relationship graph. For instance, as shown in FIG. 10, provider "Dr. Grace Hopper" is connected to medical condition "generalized anxiety disorder" both directly and indirectly, i.e., "Dr. Grace Hopper" is connected to treatments (e.g., medications and therapies) that are also connected to condition "generalized anxiety disorder." The health provider matching service 200 determines 1240, for each health provider of the one or more health providers, a level of quality of medical treatment for the conditions provided by the health provider based at least in part on one or more clinical guidelines associated with the conditions and the semantic relationship graph. The health provider matching service 200 refers 1250 one of the health providers to the patient based at least in part on the levels of quality of medical treatment.

In an example use case of the process in FIG. 12, and based on the embodiments shown in FIG. 3A through FIG. 11, the health provider matching service 200 receives a request from a laptop client device 110 submitted by a nurse treating a patient to match a therapist to the patient. The patient has been feeling nauseated and tingling in the hands, and thus the nurse inputs the terms "nauseated" and "tingling in the hands" to the health provider matching service 200 via the laptop. The health provider matching service 200 identifies that the term "nauseated" is associated with the key term nausea 510 (in FIG. 5) and the term "tingling in the hands" is associated with the key term hypoesthesia 520 (in FIG. 5). The key terms, nausea 510 and hypoesthesia 520, are both connected in the graph 1000 to the key term, generalized anxiety disorder 610. In other words, patients who have generalized anxiety disorder have typically experienced symptoms including nausea and hypoesthesia based on the graph 1000. The key term generalized anxiety disorder 610 is also connected to the key terms gabapentin 710, escitalopram 720, acceptance and commitment therapy 810, cognitive behavioral therapy 820, and Dr. Grace Hopper 490. In other words, medications including gabapentin and escitalopram have been used by patients with generalized anxiety disorder; therapies including acceptance and commitment therapy and cognitive behavioral therapy have been used by and/or recommended to patients with generalized anxiety disorder; and a provider named Dr. Grace Hopper has treated patients with generalized anxiety disorder.

Since the key term Dr. Grace Hopper 490 is associated with the providers 402 cluster, the health provider matching service 200 calculates a match score between the patient, represented by the symptoms "nauseated" and "tingling in the hands", and Dr. Grace Hopper, a provider. The match score is based on a weighted average of the strengths of each connection between the key terms nausea 510, hypoesthesia 520, and/or Dr. Grace Hopper 490. The weights applied to the strengths may be the same or different, e.g., the weights may be based on user input associated with the key term. For instance, if the patient indicates the she prefers non-medication type therapies for treatment (e.g., the nurse inputs into the software application on the laptop the patient's preference, which is received by the health provider matching service 200), then the weights applied to connection strengths of therapies 800 may be weighed more heavily than the weights applied to connection strengths of medications 700. If the calculated match score is above a threshold, the health provider matching service 200 refers Dr. Grace Hopper as a suitable therapist for the patient. The threshold may be adjusted based on the information in the graph 1000, e.g., if there is a relatively low number of providers in the graph 1000, then the threshold may be lowered to increase the likelihood that at least one provider will have a corresponding match score greater than the threshold. Finally, the health provider matching service 200 provides the nurse information from the graph 1000 associated with Dr. Grace Hopper via the laptop user interface. In some embodiments, a plurality of providers are identified from the semantic relationship graph 1000 and ranked based on the match scores. Then, the health provider matching service 200 refers the provider with the highest ranking to the patient.

In alternate embodiments, additional preferences of the patient are used by the health provider matching service 200 to calculate the match score. For example, the nurse provides the health provider matching service 200 with the patient's preference for a therapist in Mountain View, Calif. who typically treats adult patients. Since the terms Adult 441, Mountain View 446, and CA 447 are associated with the key term Dr. Grace Hopper 490, the match score, between the patient and the therapist Dr. Grace Hopper, calculated by the health provider matching service 200 will be based on the terms Adult 441, Mountain View 446, and CA 447. The match score will be greater because there is a greater degree of connection between the patient's profile (e.g., the patient's preferences) and the information associated with the therapist Dr. Grace Hopper.

Figure 13:
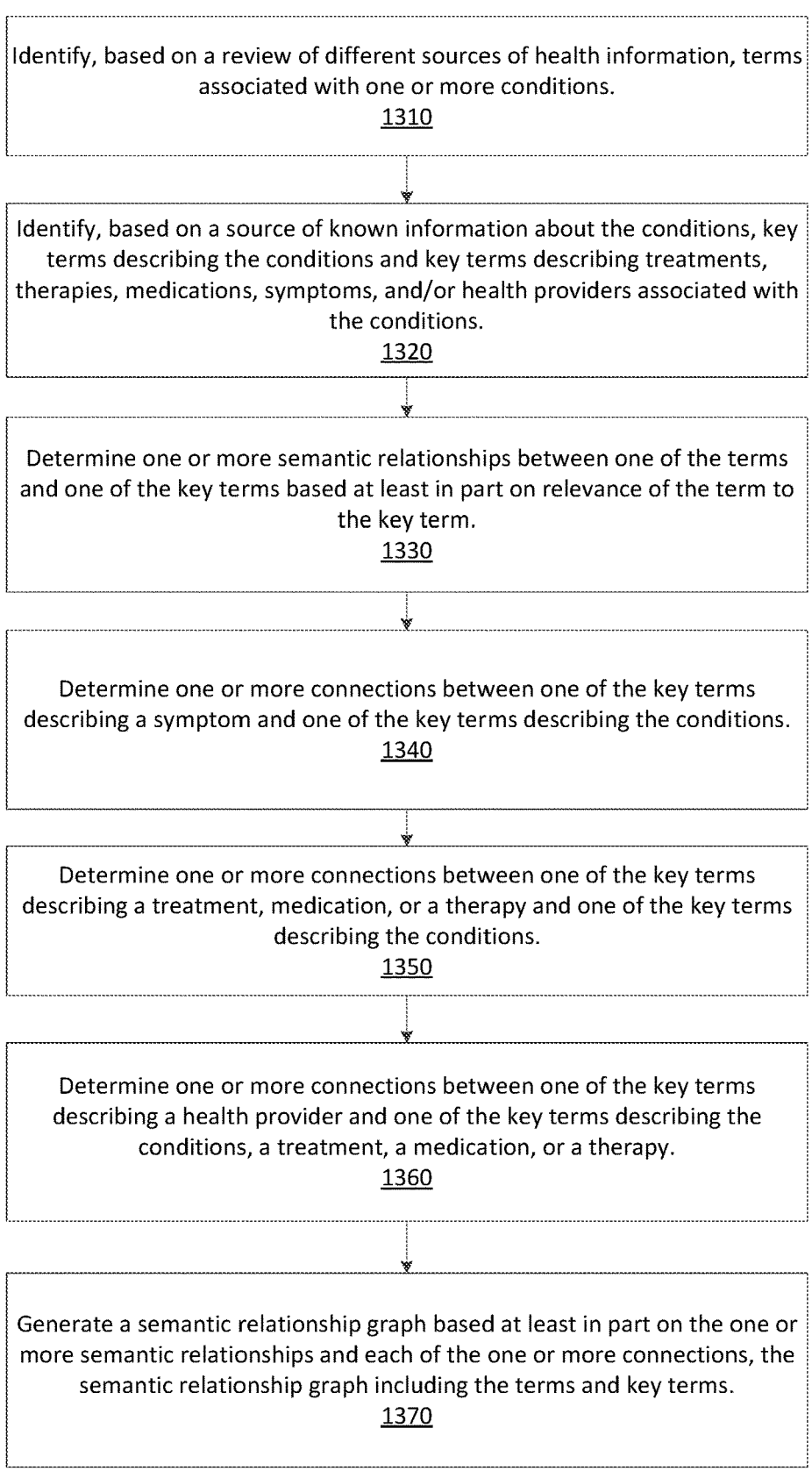
FIG. 13 is a flow chart illustrating a process for generating a semantic relationship graph within the computing environment of FIG. 1 according to one embodiment.

FIG. 13 is a flow chart illustrating a process for generating a semantic relationship graph within the computing environment of FIG. 1 according to one embodiment. The process may include different or additional steps than those described in conjunction with FIG. 13 in some embodiments or perform steps in different orders than the order described in conjunction with FIG. 13.

In the embodiment illustrated in FIG. 13, the health provider matching service 200 identifies 1310, based on a review of different sources of health information (e.g., external source 130 such as Wikipedia), a plurality of terms associated with one or more conditions. The health provider matching service 200 identifies 1320, based on a source of known information about the conditions (e.g., a health provider source 140), a plurality of key terms describing the conditions and a plurality of key terms describing treatments, therapies, medications, symptoms, and/or health providers associated with the conditions. The health provider matching service 200 determines 1330 one or more semantic relationships between a term of the plurality of terms and a key term of the plurality of key terms based at least in part on relevance of the term to the key term. For instance, the term "anxiety disorders" is relevant to the key term "generalized anxiety disorder" because both have a similar meaning. The health provider matching service 200 determines 1340 one or more connections between a key term of the plurality of key terms describing a symptom and a key term of the plurality of key terms describing the conditions. For instance, as shown in graph 1000 in FIG. 10, key term "nausea" (i.e., a symptom) is connected to key term "generalized anxiety disorder" (i.e., a condition). The health provider matching service 200 determines one 1350 or more connections between a key term of the plurality of key terms describing a treatment (e.g., a medication or a therapy) and a key term of the plurality of key terms describing the conditions. For instance, as shown in graph 1000 in FIG. 10, key term "gabapentin" (i.e., a medication) and key term "cognitive behavioral therapy" (i.e., a therapy) are connected to key term "generalized anxiety disorder." The health provider matching service 200 determines 1360 one or more connections between a key term of the plurality of key terms describing a health provider and a key term of the plurality of key terms describing the medical condition or a treatment (e.g., a medication or a therapy). For instance, as shown in graph 1000 in FIG. 10, key term "Dr. Grace Hopper" (i.e., a provider) is connected to key term "generalized anxiety disorder." The health provider matching service 200 generates 1370 a semantic relationship graph (e.g., graph 1000 in FIG. 10) based at least in part on the one or more semantic relationships and each of the one or more connections, in which the semantic relationship graph including the plurality of terms and the plurality of key terms.

Alternative Embodiments

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable non-transitory medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method comprising:
   receiving, from a patient requesting treatment, by way of a software application instantiated at a client device of the patient, input of a preferred non-clinical personality trait of a health provider;
   receiving symptom information indicating one or more symptoms of the patient;
   identifying one or more behavioral health conditions connected to the one or more symptoms in a semantic relationship graph, the semantic relationship graph including connections between key terms describing at least one of treatments, symptoms, health providers, and behavioral health conditions;
   identifying a subset of health providers having the preferred non-clinical personality trait, the subset of health providers being identified from one or more health providers that are described by the semantic relationship graph, connected to at least one of the one or more behavioral health conditions in the semantic relationship graph, and connected to the preferred personality trait in the semantic relationship graph based on a crawling, by a service that provides the software application, of pages of the one or more health care providers, the pages each including a personal statement of the one or more health providers, the personal statement including natural language corresponding to the preferred non-clinical personality trait;
   determining, for each health provider of the subset of health providers, a level of quality of treatment for the one or more behavioral health conditions provided by the health provider based at least in part on one or more clinical guidelines associated with the one or more behavioral health conditions and the semantic relationship graph;
   weighting the levels of quality by inputting terms of the personal statement into a machine learning model, and receiving from the machine learning model an output of a weighted representation of the level of quality for the health provider, wherein the machine learning model determines the weighted representation of the level of quality based on labeling of associated quality to candidate terms, the associated quality being determined based on a frequency with which the candidate terms are used by high quality or low quality providers, the output of the machine learning model based on data from one or more databases of frequently used terms used in the pages of the one or more health providers, the data from the databases being expanded by the machine learning model; and
   instructing the software application to output, at the client device, a display of a recommendation for a health provider of the subset of health providers to the patient based at least in part on the weighted levels of quality of treatment.

2. The method of claim 1, wherein one or more clinical guidelines associated with the one or more behavioral health conditions describe evidence-based treatment methodologies for the one or more behavioral health conditions.

3. The method of claim 1, wherein the recommendation is generated by:
   ranking the one or more health providers based on the levels of quality of treatment; and
   selecting a health provider of the one or more health providers with the highest ranking to the patient.

4. The method of claim 1, wherein the recommendation is generated by categorizing each health provider of the one or more health providers as a high quality provider or a low quality provider, and wherein the referring is based at least in part on the categorization.

5. The method of claim 1, wherein determining the levels of quality of treatment comprises:
   identifying one or more terms describing at least one of treatments and symptoms associated with the one or more behavioral health conditions, the identified one or more terms having been used by a plurality of health providers known to provide high quality treatment for the one or more behavioral health conditions; and
   associating, in the semantic relationship graph, information indicating a high quality with the identified one or more terms,
   wherein referring the health provider of the one or more health providers to the patient is further based on the association.

6. A computer-implemented method comprising:
   identifying, based on a review of different sources of health care information, a plurality of terms associated with one or more behavioral health conditions;
   identifying, based on a source of known information about the one or more behavioral health conditions, a plurality of key terms describing the one or more mental health conditions and a plurality of key terms describing at least one of treatments, symptoms, and health providers associated with the one or more behavioral health conditions;

determining one or more semantic relationships between a term of the plurality of terms and a key term of the plurality of key terms based at least in part on relevance of the term to the key term;

determining one or more connections between a key term of the plurality of key terms describing a symptom and a key term of the plurality of key terms describing the one or more behavioral health conditions;

determining one or more connections between a key term of the plurality of key terms describing a treatment and a key term of the plurality of key terms describing the one or more behavioral health conditions;

determining one or more connections between a key term of the plurality of key terms describing a health provider and a key term of the plurality of key terms describing the one or more behavioral health conditions or a treatment;

crawling pages of each described health provider, the pages each including a personal statement of their respective described health provider, the personal statement including natural language corresponding to the preferred non-clinical personality trait;

identifying a respective non-clinical personality trait of each described health provider based on the crawling, and generating a link between each described health provider and their respective non-clinical personality trait;

generating a semantic relationship graph based at least in part on the one or more semantic relationships and each of the one or more connections and each link between each described health provider and their respective personality trait, the semantic relationship graph including the plurality of terms and the plurality of key terms; and outputting information from the semantic graph responsive to receiving a request, from a client device of a patient, of a health care provider having a specified non-clinical personality trait to treat a symptom, wherein the information is additionally modified by inputting terms of personal statements of health care providers having the specified non-clinical personality trait into a machine learning model, and receiving from the machine learning model an output of a representation of the level of quality for the health provider, wherein the machine learning model determines the representation of the level of quality based on labeling of associated quality to candidate terms, the associated quality being determined based on a frequency with which the candidate terms are used by high quality or low quality providers, the output of the machine learning model based on data from one or more databases of frequently used terms used in the pages of the one or more health providers, the data from the databases being expanded by the machine learning model.

7. The method of claim 6, wherein the semantic relationship graph is represented by a tree graph structure, the tree graph structure comprising nodes connected by edges, and wherein the nodes store the plurality of terms and the plurality of key terms.

8. The method of claim 6, wherein generating the semantic relationship graph comprises determining a closeness score between an identified term of the plurality of terms and a corresponding key term of the plurality of key terms, the closeness score based on similarity in meaning between the identified term and the corresponding key term.

9. The method of claim 8, wherein determining the closeness score between the identified term and the corresponding key term comprises:

parsing the identified term and the corresponding key term each into one or more words;

comparing the one or more words associated with the identified term and the one or more words associated with the corresponding key term; and computing the closeness score between the identified term and the corresponding key term based on the comparison.

10. The method of claim 6, wherein the semantic relationship graph connects symptoms of the one or more behavioral health conditions to health providers who treat the one or more behavioral health conditions, allowing a patient having the symptoms to be matched with a health provider best suited to treating the patient and their possible behavioral health conditions.

11. A non-transitory computer readable medium configured to store instructions, the instructions when executed by a processor cause the processor to:

receive, from a patient requesting treatment, by way of a software application instantiated at a client device of the patient, input of a preferred personality trait of a health provider;

receive symptom information indicating one or more symptoms of the patient;

identify one or more behavioral health conditions connected to the one or more symptoms in a semantic relationship graph, the semantic relationship graph including connections between key terms describing at least one of treatments, symptoms, health providers, and behavioral health conditions;

identify a subset of health providers having the preferred non-clinical personality trait, the subset of health providers being identified from one or more health providers that are described by the semantic relationship graph, connected to at least one of the one or more behavioral health conditions in the semantic relationship graph, and connected to the preferred personality trait in the semantic relationship graph based on a crawling, by a service that provides the software application, of pages of the one or more health care providers, the pages each including a personal statement of the one or more health providers, the personal statement including natural language corresponding to the preferred non-clinical personality trait;

determine, for each health provider of the subset of health providers, a level of quality of treatment for the one or more behavioral health conditions provided by the health provider, by inputting terms of the personal statement into a machine learning model, and receiving from the machine learning model an output of a representation of the level of quality for the health provider, wherein the machine learning model determines the representation of the level of quality based on labeling of associated quality to candidate terms, the associated quality being determined based on a frequency with which the candidate terms are used by high quality or low quality providers, the output of the machine learning model based on data from one or more databases of frequently used terms used in the pages of the one or more health providers, the data from the databases being expanded by the machine learning model; and instruct the software application to output, at the client device, a display of a recommendation for a health provider of the subset of health providers to the patient based at least in part on the levels of quality of treatment.

12. The non-transitory computer readable medium of claim 11, wherein one or more clinical guidelines associated with the one or more behavioral health conditions describe evidence-based treatment methodologies for the one or more behavioral health conditions.

13. The non-transitory computer readable medium of claim 11, wherein the recommendation is generated by:
ranking the one or more health providers based on the levels of quality of treatment; and
selecting a health provider of the one or more health providers with the highest ranking to the patient.

14. The non-transitory computer readable medium of claim 11, wherein one or more clinical guidelines are associated with a non-medical mental health condition and the one or more clinical guidelines describe treatment methodologies for the non-medical mental health condition.

15. The non-transitory computer readable medium of claim 11, wherein determine the levels of quality of treatment comprises:
identify one or more terms describing at least one of treatments and symptoms associated with the one or more behavioral health conditions, the identified one or more terms having been used by a plurality of health providers known to provide high quality treatment for the one or more behavioral health conditions; and
associate, in the semantic relationship graph, information indicating a high quality with the identified one or more terms,
wherein refer the health provider of the one or more health providers to the patient is further based on the association.

16. A non-transitory computer readable medium configured to store instructions, the instructions when executed by a processor cause the processor to:
identify, based on a review of different sources of health care information, a plurality of terms associated with one or more behavioral health conditions;
identify, based on a source of known information about the one or more behavioral health conditions, a plurality of key terms describing the one or more mental health conditions and a plurality of key terms describing at least one of treatments, symptoms, and health providers associated with the one or more behavioral health conditions;
determine one or more semantic relationships between a term of the plurality of terms and a key term of the plurality of key terms based at least in part on relevance of the term to the key term;
determine one or more connections between a key term of the plurality of key terms describing a symptom and a key term of the plurality of key terms describing the one or more behavioral health conditions;
determine one or more connections between a key term of the plurality of key terms describing a treatment and a key term of the plurality of key terms describing the one or more behavioral health conditions;
determine one or more connections between a key term of the plurality of key terms describing a health provider and a key term of the plurality of key terms describing the one or more behavioral health conditions, or a treatment;
crawl pages of each described health provider, the pages each including a personal statement of their respective described health provider, the personal statement including natural language corresponding to the preferred non-clinical personality trait;
identify a respective non-clinical personality trait of each described health provider based on the crawling, and generating a link between each described health provider and their respective non-clinical personality trait;
generate a semantic relationship graph based at least in part on the one or more semantic relationships and each of the one or more connections and each link between each described health provider and their respective personality trait, the semantic relationship graph including the plurality of terms and the plurality of key terms; and
output information from the semantic graph responsive to receiving a request, from a client device of a patient, of a health care provider having a specified personality trait to treat a symptom, wherein the information is additionally modified by inputting terms of personal statements of health care providers having the specified non-clinical personality trait into a machine learning model, and receiving from the machine learning model an output of a representation of the level of quality for the health provider, wherein the machine learning model determines the representation of the level of quality based on labeling of associated quality to candidate terms, the associated quality being determined based on a frequency with which the candidate terms are used by high quality or low quality providers, the output of the machine learning model based on data from one or more databases of frequently used terms used in the pages of the one or more health providers, the data from the databases being expanded by the machine learning model.

17. The non-transitory computer readable medium of claim 16, wherein the semantic relationship graph is represented by a tree graph structure, the tree graph structure comprising nodes connected by edges, and wherein the nodes store the plurality of terms and the plurality of key terms.

18. The non-transitory computer readable medium of claim 16, wherein generate the semantic relationship graph comprises determine a closeness score between an identified term of the plurality of terms and a corresponding key term of the plurality of key terms, the closeness score based on similarity in meaning between the identified term and the corresponding key term.

19. The non-transitory computer readable medium of claim 18, wherein determine the closeness score between the identified term and the corresponding key term comprises:
parse the identified term and the corresponding key term each into one or more words;
compare the one or more words associated with the identified term and the one or more words associated with the corresponding key term; and
compute the closeness score between the identified term and the corresponding key term based on the comparison.

20. The non-transitory computer readable medium of claim 16, wherein the semantic relationship graph connects symptoms of the one or more behavioral health conditions to health providers who treat the one or more behavioral health conditions, allowing a patient having the symptoms to be matched with a health provider best suited to treating the patient.

* * * * *